(12) United States Patent
Bublewitz et al.

(10) Patent No.: US 9,168,108 B2
(45) Date of Patent: Oct. 27, 2015

(54) DISPENSING DEVICE

(75) Inventors: Alexander Bublewitz, Herborn (DE); Matthias Suchan, Hachenburg (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 752 days.

(21) Appl. No.: 12/679,025

(22) PCT Filed: Sep. 17, 2008

(86) PCT No.: PCT/EP2008/007768
§ 371 (c)(1),
(2), (4) Date: Oct. 11, 2010

(87) PCT Pub. No.: WO2009/036962
PCT Pub. Date: Mar. 26, 2009

(65) Prior Publication Data
US 2011/0114668 A1    May 19, 2011

(30) Foreign Application Priority Data

Sep. 19, 2007  (DE) .................. 10 2007 044 983
Jun. 11, 2008  (DE) .................. 20 2008 007 801 U

(51) Int. Cl.
| | | |
|---|---|---|
| B67D 7/78 | (2010.01) |
| A61C 5/06 | (2006.01) |
| A61C 9/00 | (2006.01) |
| B05C 17/005 | (2006.01) |

(52) U.S. Cl.
CPC ............... *A61C 5/062* (2013.01); *A61C 5/064* (2013.01); *A61C 9/0026* (2013.01); *B05C 17/00506* (2013.01); *B05C 17/00563* (2013.01); *B05C 17/00593* (2013.01)

(58) Field of Classification Search
CPC ...................... B05C 17/00553; A61C 5/064
USPC ........... 222/137, 136, 134, 135, 145.6, 145.5, 222/386, 391, 309, 39, 41, 43
See application file for complete search history.

(56) References Cited

U.S. PATENT DOCUMENTS

| | | | | |
|---|---|---|---|---|
| 3,248,014 A | * | 4/1966 | Gill ............................. 222/137 |
| 3,738,535 A | * | 6/1973 | Nicholls ....................... 222/137 |
| 4,538,920 A | * | 9/1985 | Drake ......................... 366/181.5 |
| 4,690,306 A | | 9/1987 | Staheli |

(Continued)

FOREIGN PATENT DOCUMENTS

| | | |
|---|---|---|
| DE | 103 37 789 A1 | 9/2005 |
| DE | 10 2005 002 850 A1 | 8/2006 |

(Continued)

OTHER PUBLICATIONS

Translation of JP 2006 151445A dated Jul. 9, 2013.

*Primary Examiner* — Paul R Durand
*Assistant Examiner* — Jeremy W Carroll
(74) *Attorney, Agent, or Firm* — McDonnell Boehnen Hulbert & Berghoff LLP

(57) ABSTRACT

A dispensing device with at least one container for the accommodation of components to be dispensed, with an applicator that can be releasably fixed to and/or on the at least one container and with a coupling means for releasable fixing of the applicator to at least one container. The coupling means may include at least one spring arm which has a radially pivotable free end for locking the applicator in place on at least one container and may further comprise a moveable locking ring.

9 Claims, 13 Drawing Sheets

(56) References Cited

U.S. PATENT DOCUMENTS

Figure 1:
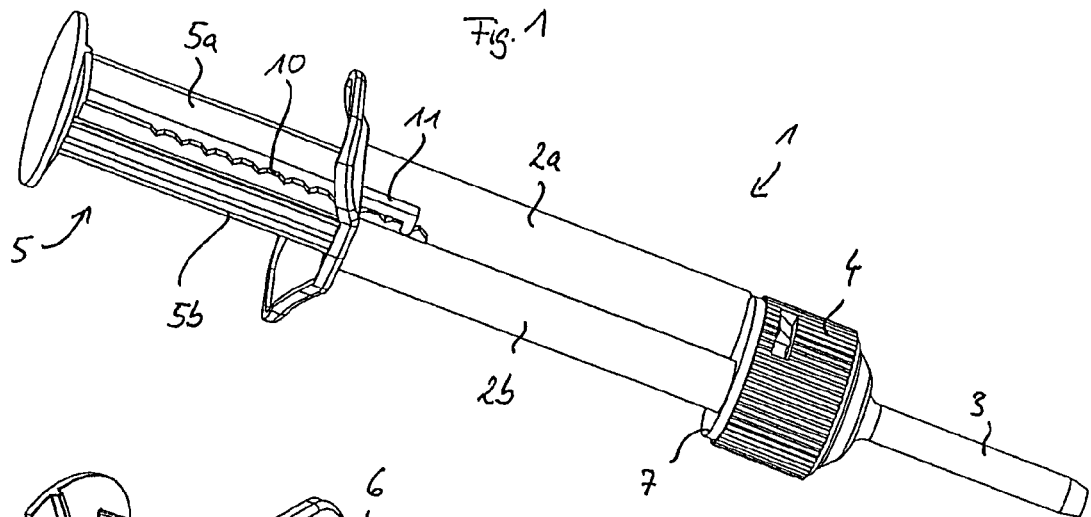

| | | | |
|---|---|---|---|
| 4,915,695 A * | 4/1990 | Koobs | 604/191 |
| 5,065,906 A | 11/1991 | Maeder | |
| 5,152,432 A * | 10/1992 | De Laforcade | 222/145.1 |
| 5,549,561 A * | 8/1996 | Hjertman | 604/131 |
| 5,647,515 A * | 7/1997 | Zwijnenberg et al. | 222/389 |
| 6,135,631 A * | 10/2000 | Keller | 366/339 |
| 7,316,330 B2 | 1/2008 | Muller et al. | |
| 7,367,475 B2 | 5/2008 | Horth et al. | |
| 7,497,355 B2 * | 3/2009 | Horner et al. | 222/137 |
| 7,882,983 B2 | 2/2011 | Reidt et al. | |
| 2004/0104249 A1 * | 6/2004 | Horth et al. | 222/145.6 |
| 2006/0157508 A1 | 7/2006 | Suchan et al. | |
| 2007/0051750 A1 * | 3/2007 | Suchan et al. | 222/137 |
| 2007/0090079 A1 * | 4/2007 | Kelller | 215/211 |
| 2007/0164047 A1 * | 7/2007 | Reidt et al. | 222/137 |
| 2007/0166660 A1 | 7/2007 | Peuker et al. | |
| 2007/0175921 A1 | 8/2007 | Keller | |
| 2007/0228076 A1 * | 10/2007 | Horner et al. | 222/135 |
| 2008/0083782 A1 * | 4/2008 | Heusser et al. | 222/145.5 |

FOREIGN PATENT DOCUMENTS

| | | |
|---|---|---|
| DE | 10 2005 041 961 B4 | 8/2007 |
| EP | 0 213 073 A1 | 8/1986 |
| EP | 0 787 534 A1 | 8/1997 |
| EP | 0787535 A1 | 8/1997 |
| EP | 0 723 807 B1 | 9/2001 |
| EP | 1 389 448 A1 | 2/2004 |
| EP | 1 430 959 A2 | 6/2004 |
| JP | H09182760 A | 7/1997 |
| JP | H09216698 A | 8/1997 |
| JP | 2003341749 A | 12/2003 |
| JP | 2006151445 A | 6/2006 |
| WO | 2004/009249 A1 | 1/2004 |
| WO | 2005/016170 A2 | 2/2005 |
| WO | 2005/016783 A1 | 2/2005 |
| WO | 2005/021394 A2 | 3/2005 |
| WO | 2006/005213 A1 | 1/2006 |
| WO | 2006073690 A2 | 7/2006 |
| WO | 2007003063 A1 | 1/2007 |

\* cited by examiner

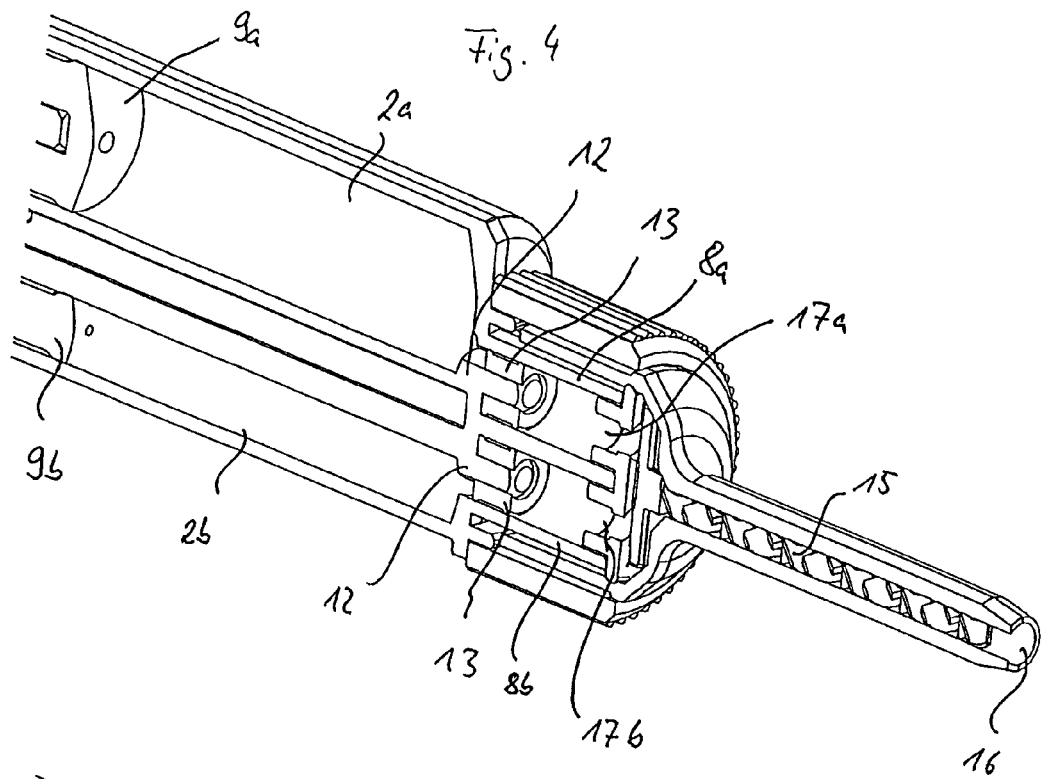
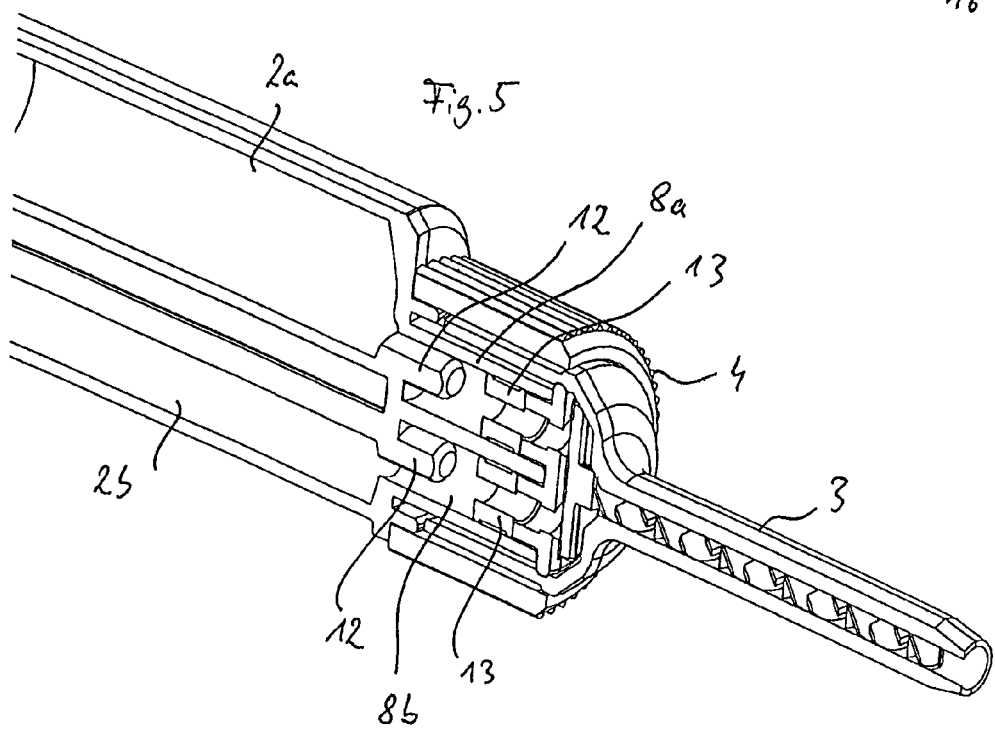

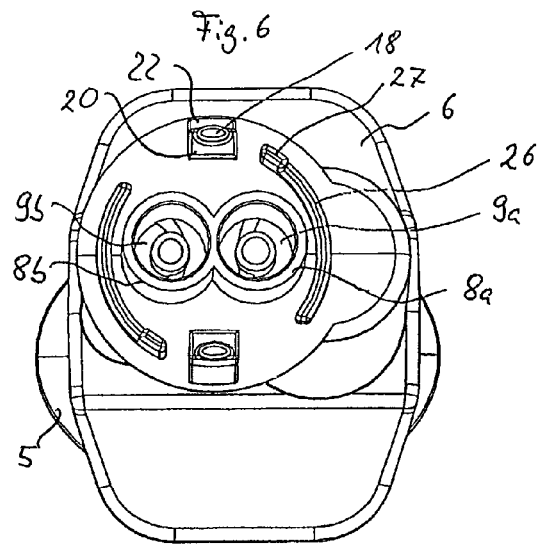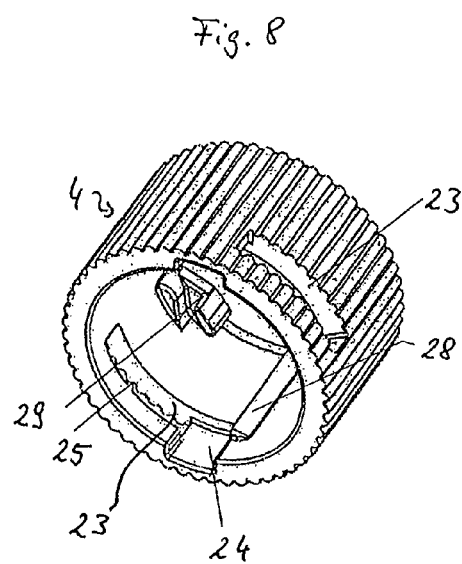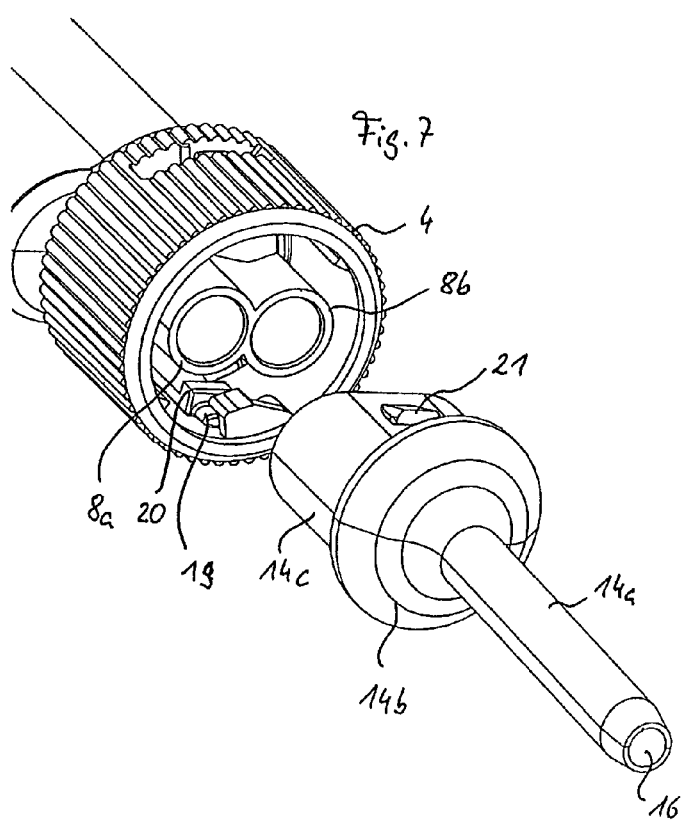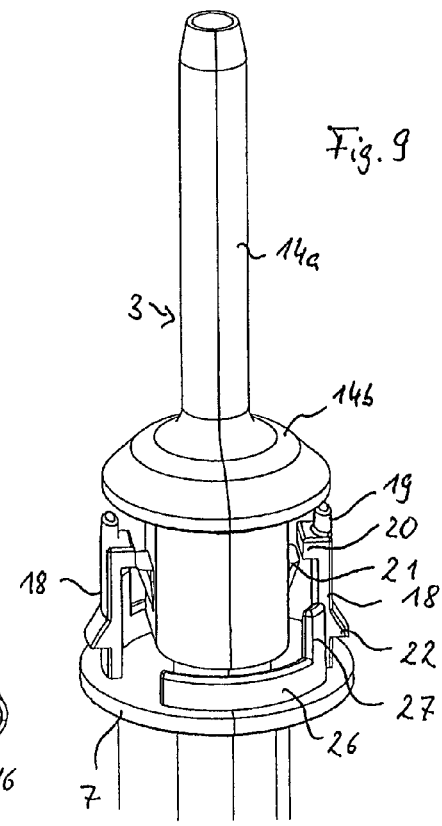

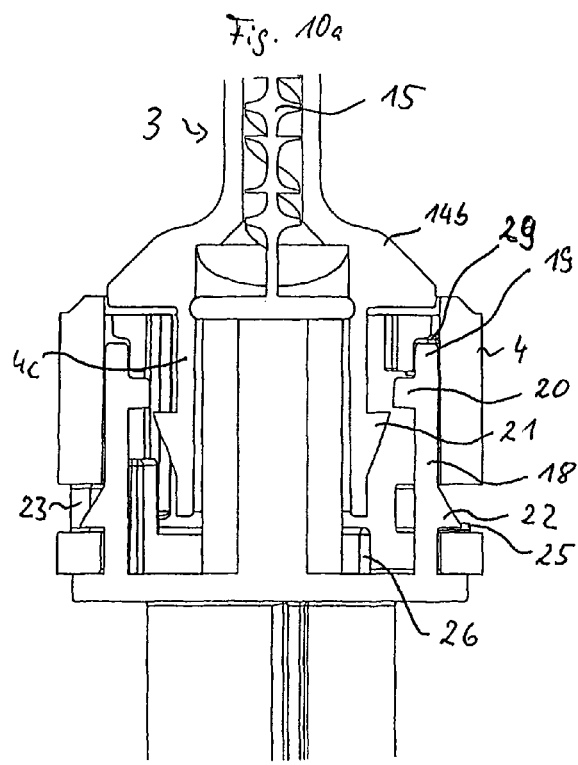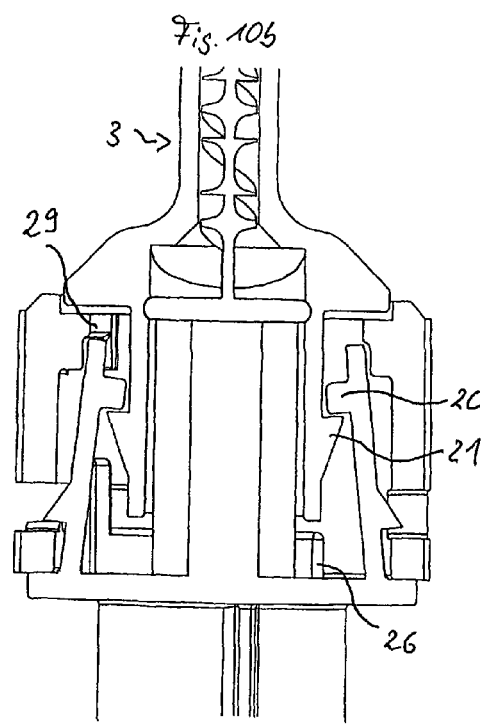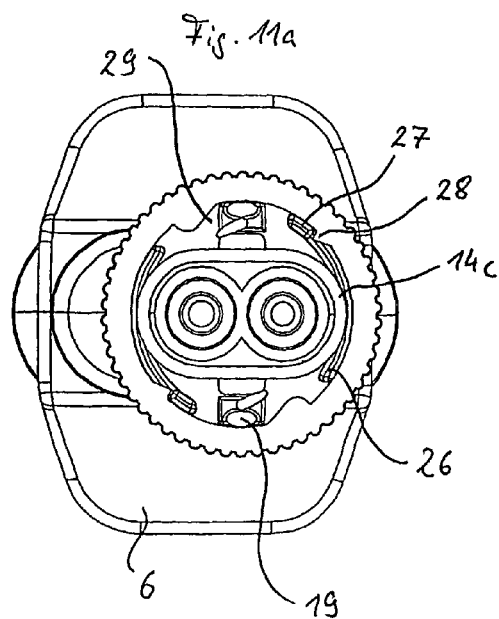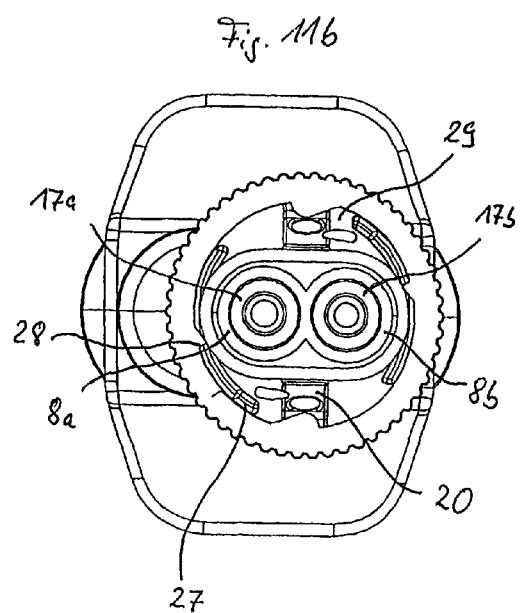

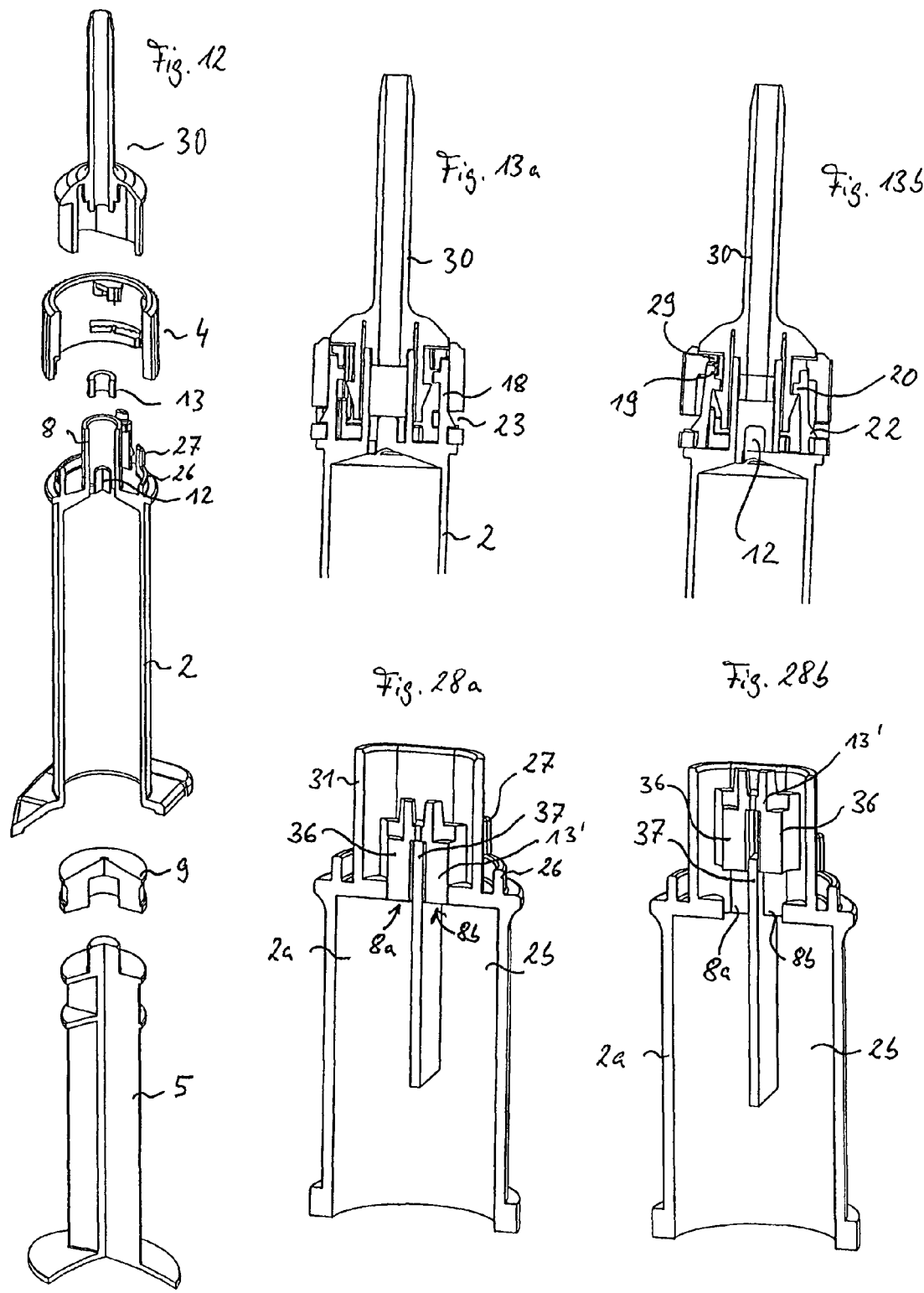

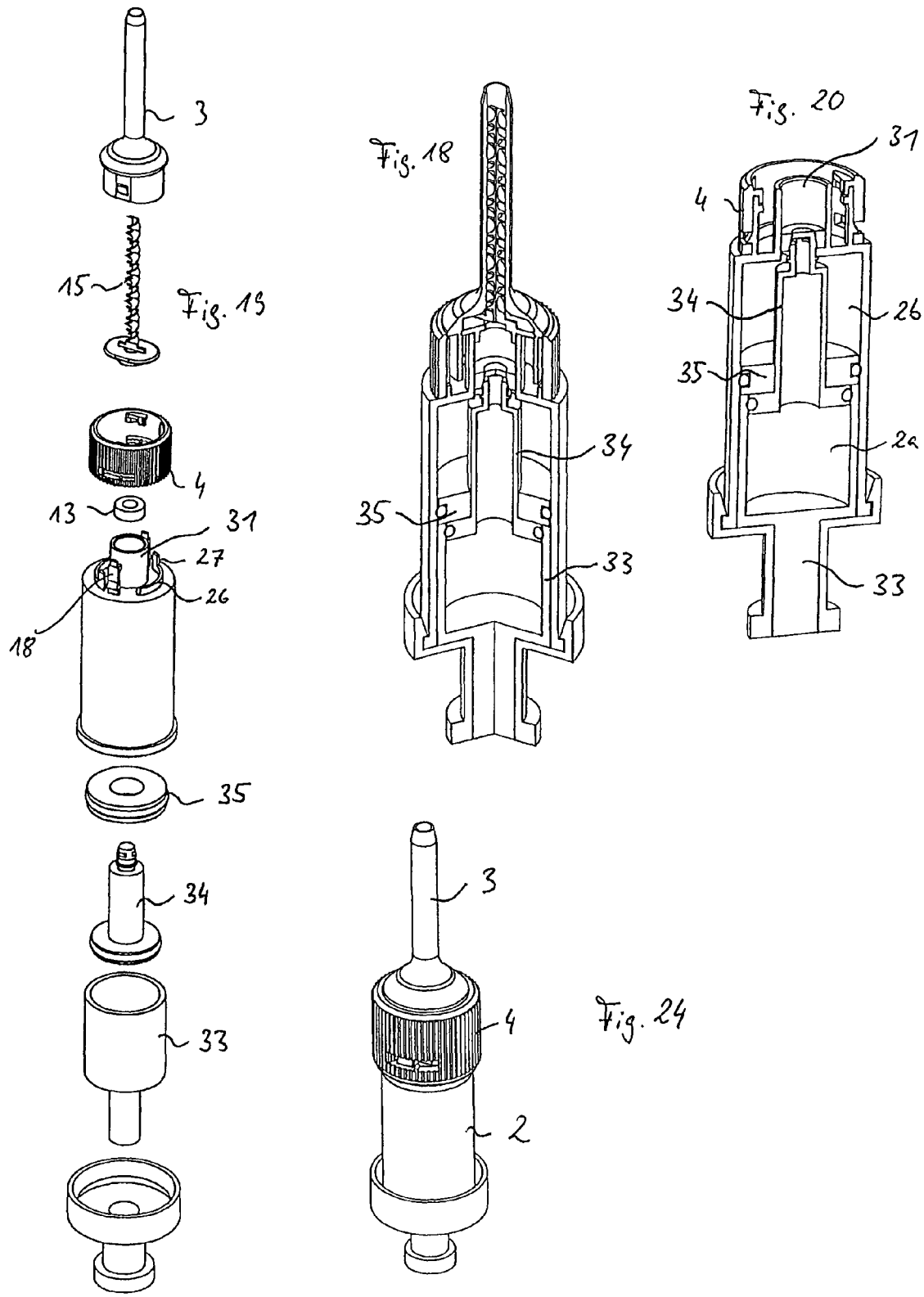

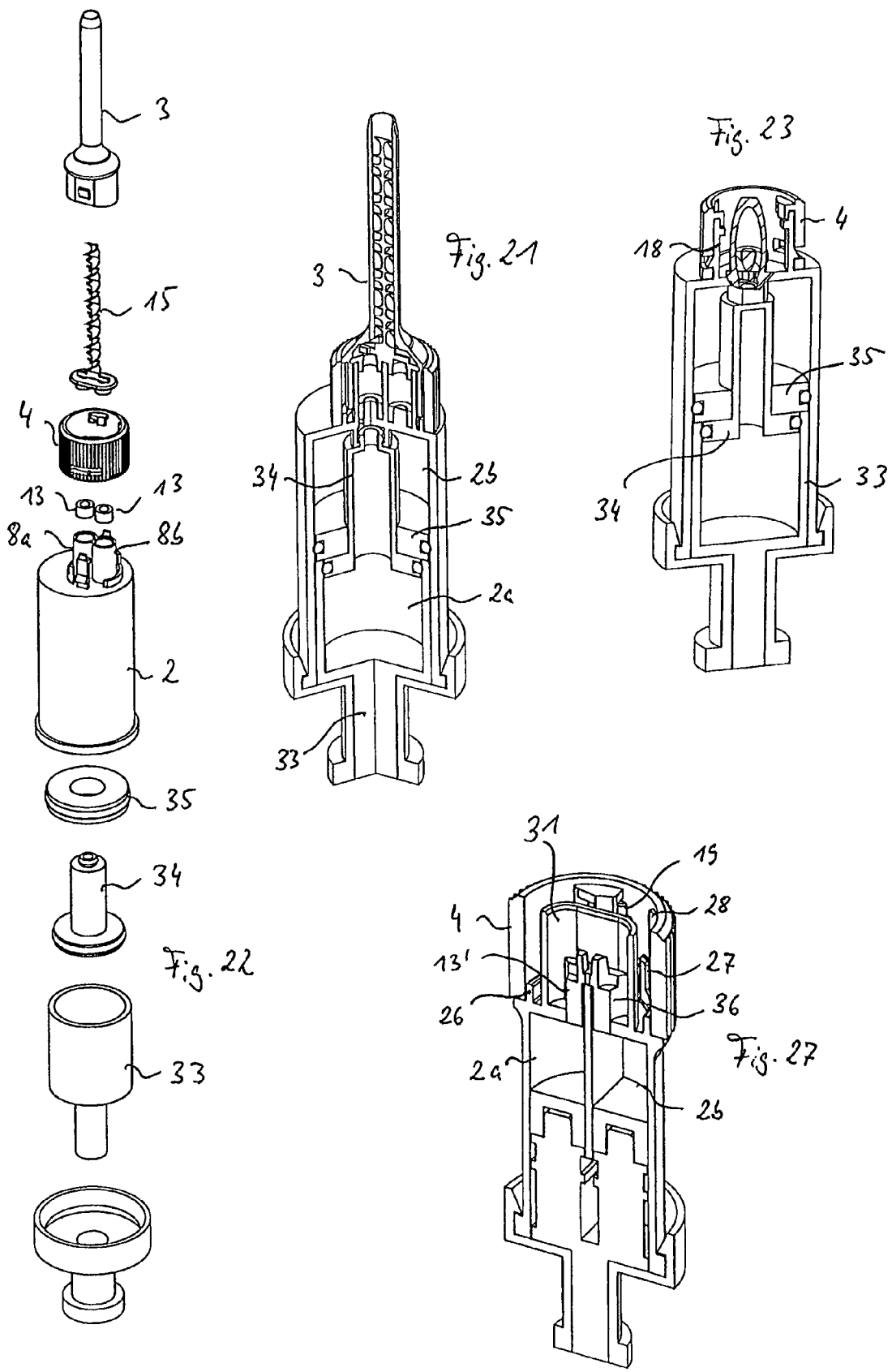

DISPENSING DEVICE

The invention relates to a dispensing device with at least one container for the accommodation of components to be dispensed, with an applicator which can be releasably fixed to a container, and with a coupling means for releasable fixing of the applicator to a container.

A dispensing device of this type is known from DE 10 2005 002 850 A1, in the case of which the coupling means is formed by a rockably mounted locking arm which can be moved from a position which frees the mixer into a position which locks the mixer in place by means of axial displacement of a locking element. A reliable locking and freeing of the mixer is thereby enabled. In the case of very small cartridges, the operation of the locking ring can, however, be found to be capable of further improvement, so that this dispensing device is particularly suitable for cartridges in which a quantity of the components sufficient for use a number of times is accommodated.

A dispensing device for a single use is known from WO 2006/005213 A1, in the case of which a mixer before the device is used, i.e. at the factory, can be put on a distal outlet region of a double cartridge and can be locked in place by rotating an annular attachment part, which is designed in one piece with the mixer, in the manner of a bayonet lock. A further embodiment of WO 2006/005213 A1 shows a dispensing device, in the case of which the mixer is secured in place on a double cartridge by means of catch hooks. If the mixer is pulled a small distance away from the double cartridge and out of a position pressed against the double cartridge, sealing plugs are released from the discharge openings of the double cartridge in order to allow the components accommodated in the cartridges to be discharged. The securing in place of the mixer on the double cartridge is chosen to be such that the mixer does not come off the double cartridge in the process. A complete removal and replacement of the mixer is not provided, rather the mixer is fixed in such a manner that it can no longer be separated from the cartridge without the use of destructive force.

A similar device is also known from EP 1 430 959 A2, in the case of which a cap which is in one piece with a mixer is clicked onto a discharge end of a double cartridge. As a result of the pressure of the components when being pressed out, the closure cap together with the mixer can be advanced so far in the distal direction that the discharge openings of the cartridges are unblocked.

Further, a dispensing opening for a single use is also described in EP 1 389 448 A1, in the case of which a mixer is secured in place on a double-chambered syringe. The mixer is, in this case, first fixed on the double-chambered syringe in a first stage in such a manner, that the discharge openings of the double-chambered syringe are sealed and the mixer cannot come off the discharge syringe. If the mixer is then advanced in the direction of the double-chambered syringe and secured in place, the discharge openings of the double-chambered syringe are unblocked at the same time. The sealing is, in the case of this known device, further found to be worthy of improvement.

The previously described dispensing devices, in the case of which the mixer is held on the containers by means of a securing in place, exhibit the disadvantage that they are usually only suitable for a single use, without the mixer offering the possibility of being replaced. As, in most use cases, the components to be mixed with one another harden in the mixer even after a short time, the entire residual contents of the container must be discarded if it is not possible to put on a new mixer.

In order to allow the mixer to be replaced, bayonet locks are provided in many use cases, using which, a mixer can be locked in place on containers and freed again. An arrangement of this type is known from EP 0 723 807 B1 which describes a mixer which can be attached to a double cartridge. The mixer is additionally provided with a rotatable locking ring which bears bayonet tongues which can be brought into engagement with bayonet claws on the container by rotating the locking ring relative to the double cartridge, so that the mixer is held securely on the double cartridge. When the locking ring is rotated back, the mixer allows itself to be released from the double cartridge again.

Bayonet locks of this type have the disadvantage, however, that they are generally only suitable for dispensing comparatively runny components. If more viscous components are to be dispensed with a correspondingly higher discharge pressure, the danger exists that the bayonet claws on the containers expand radially outwards, so that the mixer can come off during operation. Additionally, bayonet locks frequently stick, so that, to some extent, it is difficult to open them without components escaping undesirably.

Additionally, reusable systems usually must be delivered with a separate closure cap which is removed by the user before the first use. This causes an additional effort, both in the case of production and in the case of handling.

It is an object of the present invention to provide a dispensing device of the type mentioned above, which allows a releasable and secure locking of the mixer to the containers and which, at the same time, stands out on account of its particularly simple handling.

This object is essentially achieved according to the invention, in that a dispensing device, with at least one essentially rigid container, which is filled with a component to be dispensed and is closed with respect to the surroundings in a sealed manner by means of at least one sealing element, with an opening means for defined opening of the at least one sealing element as a function of the internal pressure in the respective container (i.e. the defined opening is effected by the internal pressure), with a coupling means for the releasable fixing of an applicator to and/or on the at least one container, and with an applicator which is releasably fixed by means of the coupling means, is provided. A dispensing device of this type stands out with respect to the known devices by means of a markedly improved handling, as a user can use the dispensing device according to the invention immediately, without further activation and/or installation steps. In other words, it is no longer necessary, in the case of the device according to the invention, to put an applicator, which is configured, for example, as a mixer, onto a container, or to open a container in a separate step. Additionally, a separate closure cap is not necessary in the case of the device according to the invention. In spite of this, it is further possible to replace the applicator, in the event that the quantity of the component which is contained in the at least one container is not completely used up during the first use.

The abovementioned object is further achieved, alternatively or additionally to the previously mentioned features, with a dispensing device of the type mentioned above, in which the coupling means has at least one spring arm, which has a radially pivotable free end for locking the applicator in place on the containers, and comprises a moveable locking ring, in that the coupling means of the dispensing device has a locking ring which is rotatably, but not axially-displaceably fixed to at least one container, wherein the locking ring has a groove (guide and/or steering) which acts together (co-operates) with the spring arm to control the pivot movement of the spring arm as a result of a rotation of the locking ring. In other words, rotating the locking ring either positions the spring arm against the mixer or similar applicator in such a manner that the latter is locked in place on at least one container, or guides the spring arm radially outwards away from the applicator in a defined manner, so that the applicator is freed. The rotational movement for locking in place or freeing the applicator stands out on account of a particularly simple handling, even in the case of very small dispensing devices.

In accordance with a first embodiment of the invention, the dispensing device has only one container, to which a (hollow) needle, a discharge spout, a sponge or a brush is releasably fixed as an applicator. As an alternative to this, it is also possible to provide a plurality of containers. In the case of a dispensing device with at least two containers, a mixer, a (hollow) needle, a discharge spout, a sponge or a brush can be releasably fixed to the containers as an applicator. Further advantageous configurations of the invention are described hereinafter by way of example with reference to an embodiment with at least two containers and a mixer as an applicator. In the case of these exemplary embodiments, however, in each case and according to the invention, only one container may be provided and/or the mixer may be replaced with another suitable applicator.

In the case of a dispensing device according to the invention, the containers in each case preferably have a distal discharge opening and a proximal opening opposite the latter as well as a discharge plunger which can be displaced between these openings, so that a component can be discharged from the container through the discharge opening by means of the axial movement of the discharge plunger. The mixer can here have a fixing end on the container side, with inlet openings and an outlet opening opposite the latter, and can be releasably fixable to the containers in such a manner that, in the state in which it is fixed to the containers, in each case, one of the inlet openings is in flow connection with one of the discharge openings. In accordance with a preferred embodiment of the invention, the coupling means is equipped with two mutually opposite spring arms, the free ends of which arms can be pivoted towards each other in the radial direction, as a result of a rotation of the locking ring, to lock the mixer in place on the containers. Conversely, the mixer can be released by reversed rotation of the locking ring, wherein the free ends of the spring arms are pivoted radially outwards away from each other as a result of this rotation of the locking ring. The mixer can be locked in place on the containers particularly securely by means of the two mutually opposite spring arms.

A particularly simple design of the dispensing device according to the invention, with a small number of components to be connected with one another, can be achieved, in that the end of the at least one spring arm which faces away from the free end is connected integrally with at least one of the containers and/or a distal end wall of the container. In the case of this configuration of the dispensing device, the mixer is therefore locked in place directly on the containers by means of the spring arms which are integrally connected with them.

If the at least one spring arm has at least one catch for fixing the locking ring, the locking ring can be secured to the containers particularly simply. Here, it is preferred if the locking ring is equipped with at least one recess and/or at least one catch projection, which recess and catch projection are adapted to the geometry of the catch of the spring arm in such a manner that the locking ring is fixed to the at least one spring arm and therewith to the containers such that it can be rotated but cannot be axially displaced. The spring arm therefore fulfills a dual function, on the one hand of fixing the locking ring and on the other hand of securing or freeing the mixer.

It is preferred, in order to give a user the confidence that the mixer is satisfactorily locked in place and will not undesirably become detached from the containers during the discharge of the components, if the locking ring has locking means (blocking means and/or clamping means) for locking (catching and/or clicking into place), that is to say releasable fixing, of the locking ring in at least one rotational position relative to the containers. The locking means can, in this case, not only ensure that the locking ring does not undesirably become released from the set position, but furthermore also give tactile feedback to a user that the desired locking or freeing position has been reached.

It is provided, in a development of this inventive idea, that the locking ring has at least one catch projection or a catch recess within the recess for locking the locking ring in two rotational positions relative to the containers, wherein these rotational positions correspond to a position which fixes the mixer to the containers and a position which frees the mixer. In other words, a locking of the locking ring can be achieved particularly simply, in that a catch-like catch projection is formed in the, for example, slot-shaped recess of the locking ring, through which projection the catch of the spring arm must pass to arrive at one of the two end positions which effect a locking in place of the mixer and a freeing of the mixer, respectively.

The locking in place of the mixer on the containers can take place particularly simply, in that the at least one spring arm has a radially inwards facing rib, particularly in the region of its free end, and the mixer has at least one radially outwards facing catch. If the spring arm is pushed radially inwards, that is to say in the direction of the axis of rotation of the locking ring, by a rotation of the locking ring, the rib of the spring arm is positioned behind the catch of the mixer, so that the mixer is locked in place on the containers. When the rib of the spring element grips behind the catch of the mixer in this manner, particularly high axial forces can act on the mixer, without this becoming detached from the containers, as the rib of the spring arm is constantly held against the mixer by the locking ring. The spring arm can therefore not undesirably be pushed outwards, as would be possible in the case of a simple catch or snap connection.

According to a preferred embodiment of the invention, the locking ring has at least one guiding groove and the at least one spring arm has a guide projection for engaging in the guiding groove, which projection is particularly located at the free end of the spring arm, wherein the guiding groove extends along a curve in or on the locking ring, the distance of which curve from the axis of rotation of the locking ring is not constant. The combination of a guiding groove and a guide projection, which is similar to a sliding guide, has the effect that the positioning of the spring arm against the mixer and the movement of the spring arm away from the mixer are controlled in a defined manner by means of the rotation of the locking ring. Unlike in the case of a catch or snap connection, the locking in place is not dependent on a spring action of the spring arm itself, so that even fatigue of the material of the spring arm would not lead to an impairment of function. Rather, the active control of the movement of the spring arm ensures that the spring arm moves in a defined manner to lock the mixer in place or free it when the locking ring is rotated.

In order to prevent the mixer from being placed onto the container in a position of the locking ring when the spring arms are already pivoted inwards, it is preferred if the mixer has a section which can be inserted into the locking ring and which has an outer contour which is matched to the contour of the opening in the locking ring in such a manner, that the mixer can only be inserted into the locking ring in two rotational positions relative to the latter.

It is particularly preferred if the mixer will only allow itself to be inserted into the locking ring in exactly one position relative to the latter. It is thereby also ensured that the inlet openings of the mixer and the discharge openings of the container come into contact with one another in a manner in which they are correctly aligned with one another. This is particularly advantageous in the case of containers which are suitable for multiple use with a replaceable mixer or similar applicator, as a defined assignment of this type, of outlet channels or the like in the container and corresponding inlet channels or the like in the mixer, takes place. This can preferably take place by means of coding and/or alignment means which, for example, can be configured as suggested in EP 0 598 965, EP 0 723 807 or EP 0 730 913, that is to say, the coding takes place by means of projections and recesses that match one another on the mixer and the container. Alternatively or in addition to this, a defined alignment of mixer and container with one another can also be achieved, in that the contour of the outlet connecting piece and/or of outlet channels of the container and a corresponding opposite contour or inlet channels of the mixer only permit installation of the mixer in a single alignment relative to the container.

In order to produce a flow connection between the containers and the mixer, the discharge openings can, in each case, project away from the container in the distal direction, wherein the inlet openings of the mixer can be put into these discharge openings. Preferably, the inlet openings and the discharge openings are in this case adapted to one another in such a manner, that a certain sealing is achieved, so that the components to be discharged cannot escape uncontrollably between the containers and the mixer.

For transporting and storing the components in the containers, the latter are preferably hermetically sealed. At the same time, opening of the container should be made to be as simple as possible. This is achieved according to the invention, in that the containers in each case have a discharge opening, to which, in each case, a sealing plunger is assigned, which plunger can be moved, by means of the pressure of the components to be discharged, from a position which seals the discharge opening into a position which opens the discharge opening. The sealing plungers are, in other words, arranged in such a manner, that they are, by way of example, pushed out of the discharge openings by means of the pressure generated during the discharge of the components. This enables an intuitive opening of the container, without a seal or similar closure needing to be removed in a separate work step.

In order to use the dispensing device according to the invention multiply, if appropriate, also with replaceable mixers, the components should first come into contact with one another in the mixer, so that they cannot react with one another as early as in the container or its outlet channel. For this purpose, in a container with two or more chambers for accommodating different components, each chamber is, at least in the opened state of the container, assigned a separate channel for separately passing one component through into a mixer or applicator in each case. The components are therefore always conveyed into the mixer separately from one another and first come into contact with one another there.

This can preferably be achieved, in that the channels are only separated from one another by means of the displacement of a sealing plunger into the opened state of the container. Before the opening of the container, the channels need therefore not yet be completely configured or separated from one another. So, the discharge region of the container and the sealing plunger can be configured in such a manner, that the components must flow around the sealing plunger after the opening of the container, wherein the sealing plunger separates the channels from one another.

If the containers in each case have a discharge opening which is formed by a tube and which has, in sections in its interior, a peg-shaped projection, an annular space for discharging the respective component remains between the peg-shaped projection and the inner wall of the tube. In this case it is preferred if the sealing plungers are configured as rings which are placed onto the respective peg-shaped projection in a sealing manner in order to seal the discharge opening and/or the annular space, and can be displaced in the distal direction away from the respective peg-shaped projection into a position which opens the discharge opening. During transporting and storing of the components in the containers, the containers are then closed in a sealing manner at their proximal ends by the discharge plunger and at their distal ends by the sealing plunger. The annular sealing plunger seals the annular space between the peg-shaped projection and the inner wall of the tube, which defines the discharge opening. At the start of the discharge procedure, the sealing plungers are displaced in the distal direction so that they release themselves from the peg-shaped projections as a result of the pressure of the components to be discharged. This makes it possible for the components to flow first through the annular space between the peg-shaped projection and the inner wall of the tube and subsequently through the central opening of the sealing plungers in the direction of the mixer.

It is preferred here if the lengths of the peg-shaped projection and the sealing plunger are together shorter than the length of the tube. The sealing plungers can thereby be pushed sufficiently far forwards in the distal direction, so that the components can escape unhindered. The advancing movement of the sealing plungers can, for example, be limited by the inlet openings of the mixer which were put into the discharge openings.

If the opening means has a sealing plunger as sealing element, which can be displaced out of a sealed transport and storage position into an opened use position by means of the internal pressure of the component to be dispensed in the respective container, the dispensing device according to the invention can be opened intuitively with particular simplicity, without a separate closure cap or the like needing to be provided during transport or storage. In this case, an opening, which extends axially in particular, can be provided in the sealing plunger in such a manner, that the at least one component to be dispensed can only flow through this opening in the use position of the sealing plunger. The dispensing of the component therefore takes place through the opening, which preferably extends axially, in the interior of the sealing plunger. Alternatively or in addition to this, the sealing plunger can have an outer contour which is definedly smaller than the inner contour of a discharge opening, so that, at least in the use position, at least one channel-like opening is formed between the sealing plunger and the discharge opening. Therefore, in the use position of the sealing plunger, the at least one component to be dispensed flows through this channel-like opening, that is to say, the channel-like opening acts in the manner of a bypass channel in which the component laterally bypasses the sealing plunger.

In accordance with a particularly preferred embodiment of the invention, the dispensing device is configured as a double-chambered syringe with two containers, which are connected integrally with one another, and a plunger rod arrangement for simultaneously advancing the discharge plungers in the containers. Double syringes of this type are particularly suitable for discharging hardenable two component systems which are used in the dental sector. The replaceability of the mixer enables the components accommodated in the containers to be discharged in a number of different uses, without the residual contents of the container needing to be disposed of as early as after the first use. The dispensing device according to the invention is fundamentally also suitable for single uses, particularly on account of the possibility of opening it intuitively and without additional work steps.

Independently of the features described beforehand, the dispensing device according to the invention solves a further problem. A container is offered by TAH Industries, Inc., Robbinsville, USA under the name 'u-TAH™ nano', which has two chambers which are arranged coaxially with respect to one another and essentially behind one another and which can be emptied by means of a pot-like transfer plunger. This container is supplied with a closure cap which must be removed before the first use, in order, if appropriate, to fix a separate mixer or similar applicator to the container. The 'u-TAH™ nano' container has a retaining section which is suitable for connecting to a discharge gun which, by way of example, is sold under the name 'Centrix®' by Centrix, Inc., Shelton, USA. A gun of this type is also described in EP 1 256 389 A2.

Discharge guns of this type are present in almost every dental practice as manual dispensers for what are known as pre-loaded tips (PLTs) for discharging 1 component dental composites. From an economic viewpoint, it is therefore desirable to use these existing dispensers or guns for as many dental material groups as possible and in particular also for 2 component systems.

According to the invention, a container is therefore suggested, which, while offering a high degree of user-friendliness, enables secure storage of the components at the same time. This is essentially achieved with a container for storing and discharging at least two components, in particular by means of a discharge gun or the like, which container has at least two chambers for accommodating the components, a plunger means for simultaneously discharging the components from the chambers, a mixer, which is pre-installed on the container, for mixing the components which have been discharged from the chambers, and a sealing means for sealing the chambers, which can be opened without uninstalling the mixer. In this case, the plunger means has at least one plunger rod which is assigned to a plunger, which plunger rod is accommodated in a displaceably guided manner in a retaining section, which faces away from the mixer, of the container, so that the plunger rod, before the discharging of the components, is provided essentially flush with the front side of the retaining section which faces away from the mixer. The invention stands out in particular on account of the combination of a container with a mixer which is pre-installed in the delivery state, a sealing means which can be opened without uninstalling the mixer, and a transport securing device that prevents the container from being undesirably opened during transport or storage.

The last-mentioned function is achieved in that a plunger rod, which is assigned to the plunger means, is accommodated in a displaceably guided manner in a retaining section, which faces away from the mixer, of the container so that the plunger rod does not notably project out of the retaining section of the container. In other words, the end of the plunger rod essentially is flush with the front side of the retaining section which faces away from the mixer (i.e. the end of the plunger rod and the front side of the retaining section are essentially in a common plane), so that pressure cannot inadvertently be exerted. The provision of the end of the plunger rod flush with the front side of the retaining section, which faces away from the mixer, of the container is below understood to mean not only an exactly flush arrangement, but rather also that the plunger rod projects by a few millimeters, preferably not more than approximately 1 to approximately 2 mm, beyond the front side of the retaining section. In the case of this configuration, the container is also suitable for use with a discharge gun or a dispenser of the abovementioned type, for example with a 'Centrix®' gun. In contrast, it is unimportant for the function of the transport securing device whether the plunger rod is slightly set back with respect to the front side of the retaining section which faces away from the mixer. At most, this limits the possibilities for completely emptying the container.

If the mixer is pre-installed on the container in accordance with the invention, the container can be taken directly into use without time-consuming installation steps. A pre-installed mixer is understood to be a mixer, in particular a static mixer, which is already provided, in the delivery state of the container, in a position on the container which is essentially also suitable for discharging the components. This does not exclude the possibility that, if appropriate, the mixer or a mixing tube and/or a discharge tube of the mixer must be turned and/or displaced slightly relative to the container in order to open the container prior to the first use of the container. However, it is preferred if the mixer is pre-installed on the container in such a manner that the mixer is already located in its end position which is suitable for discharging the components.

Independently of the features mentioned beforehand, a further essential aspect of the present invention lies in the fact that the plunger means of the container has a transfer tappet which has a plunger rod which is guided in the retaining section of the container and actuation sections for discharging the components from the chambers connected thereto. The actuation sections can in each case interact with a plunger which can be displaced in the chambers. In accordance with a particularly preferred embodiment of the invention, the transfer tappet is configured such that each chamber of the container is assigned a separate actuation section which projects from the plunger rod in the direction of the mixer. The handling of the container according to the invention is thereby further simplified, as two or more actuation sections can be pushed forward simultaneously by means of the advance of the one plunger rod of the transfer tappet, so that all chambers can be emptied at the same time. This also simplifies the use of the container according to the invention in a discharge device, for example a discharge gun, with only one displaceable tappet. In development of this inventive idea, the plunger rod and the actuation sections of the transfer tappet can be formed integrally with one another.

The invention is explained in more detail hereinafter on the basis of an exemplary embodiment and with reference to the drawings. All described and/or pictorially represented features form the subject of the invention per se or in any desired combination, independently of their summarization in the claims or back references thereof.

Figure 2:
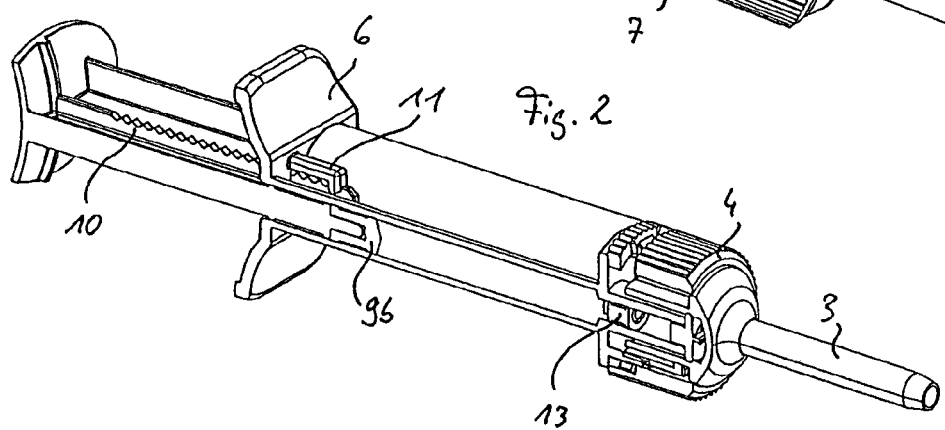
Figure 3:
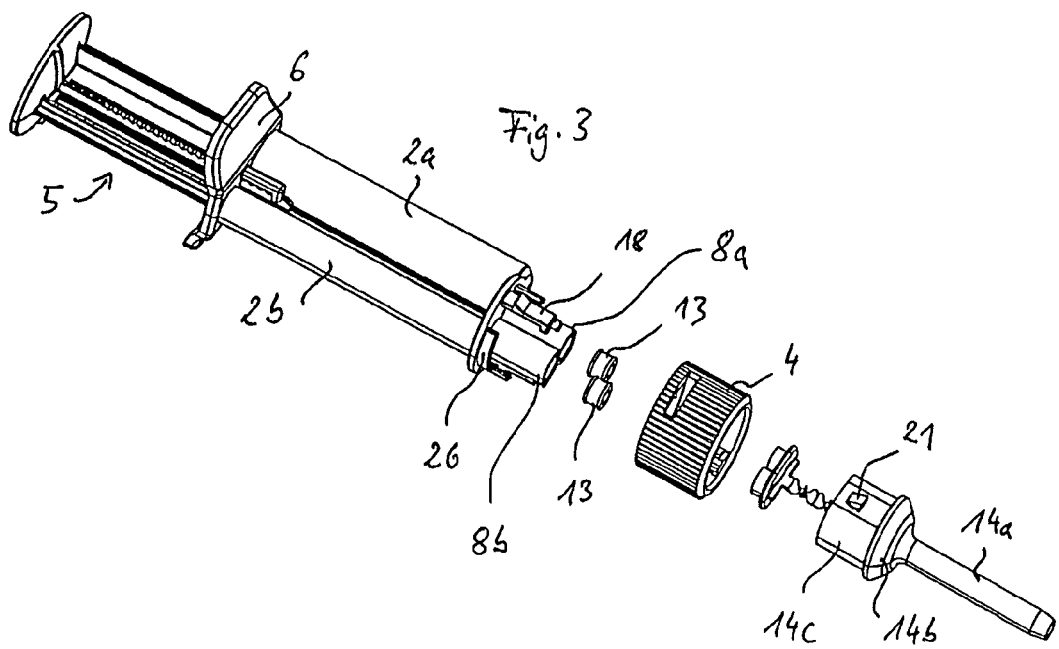
Figure 14:
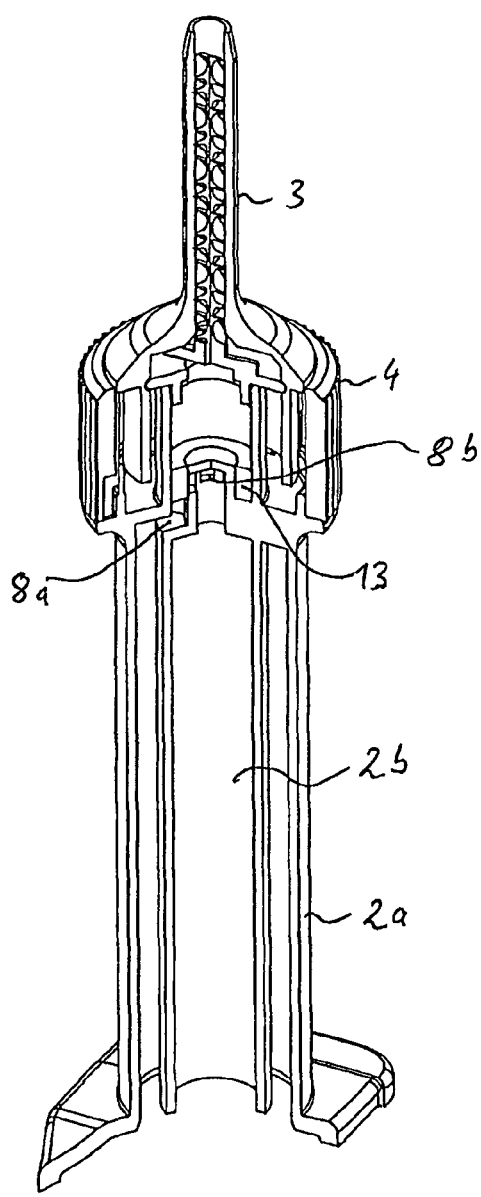
Figure 15:
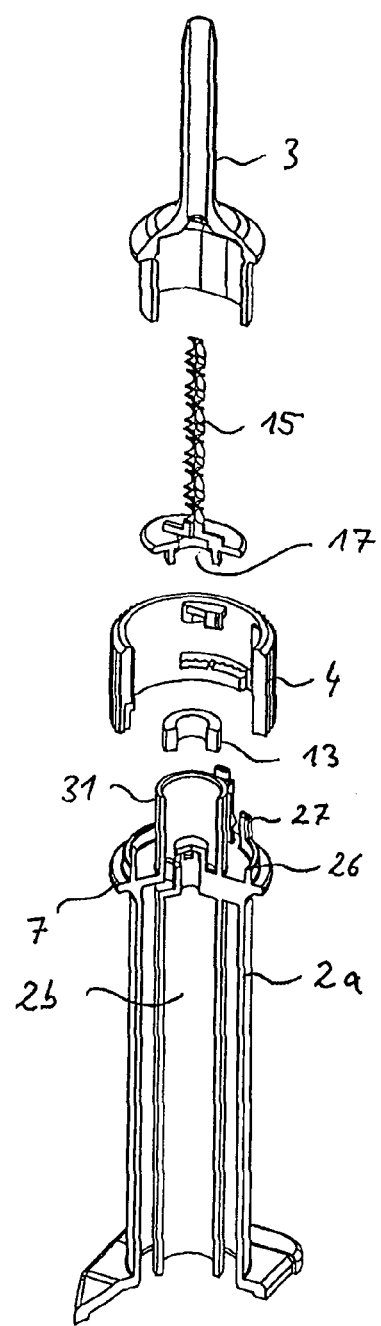
Figure 16:
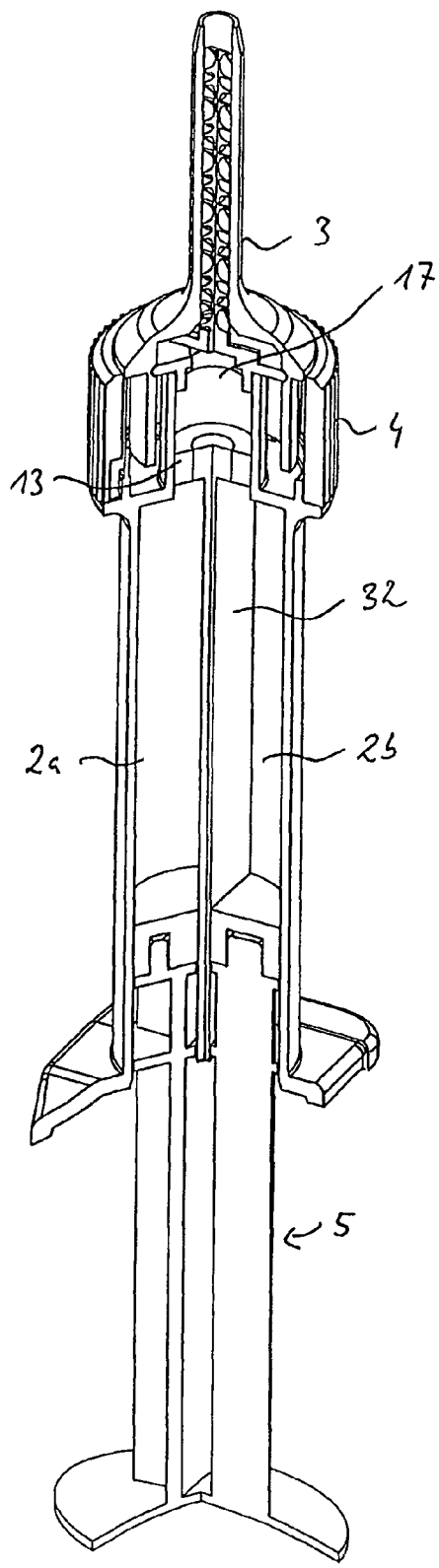
Figure 17:
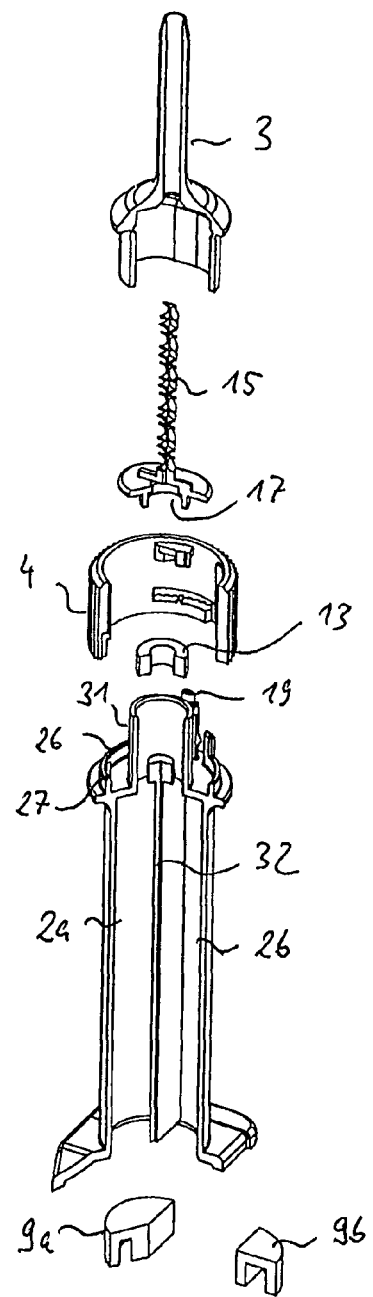
Figure 26:
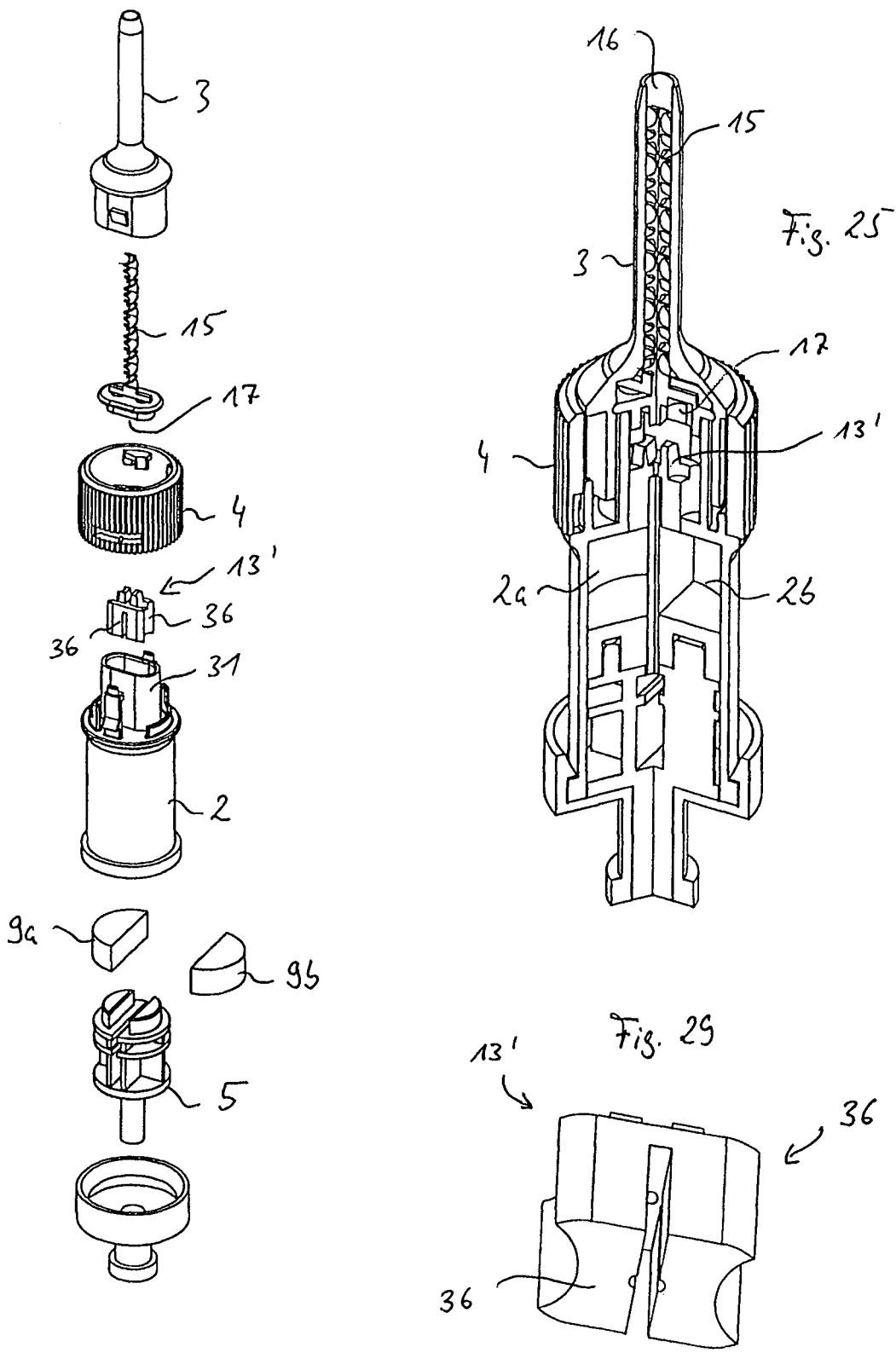
Figure 30:
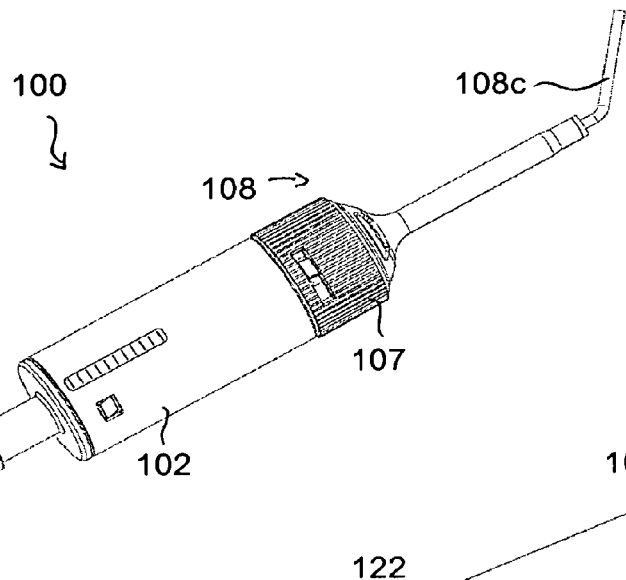
Figure 31:
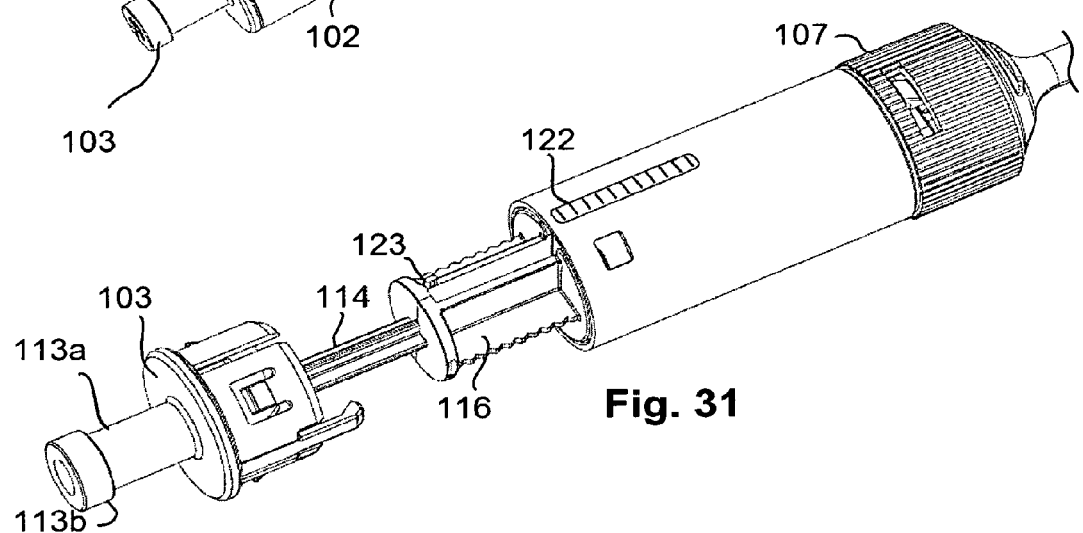
Figure 32:
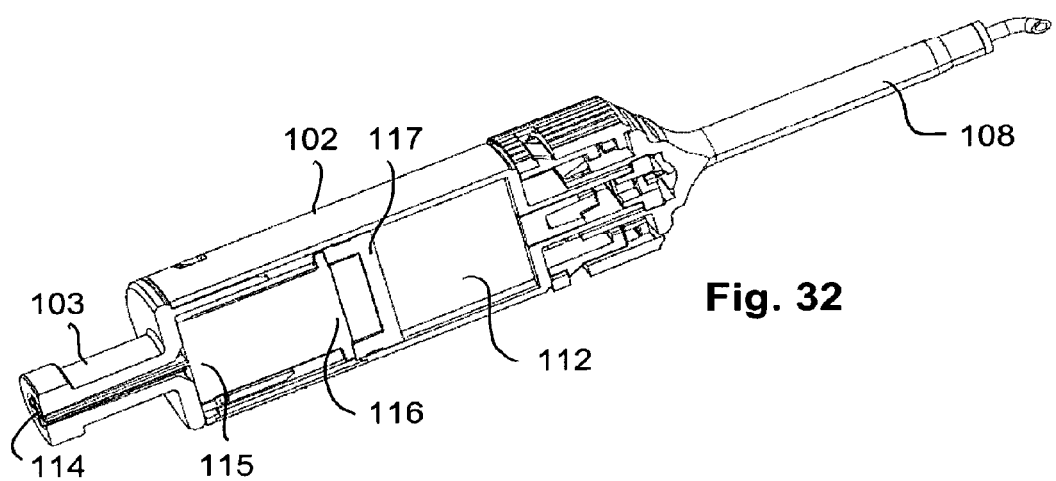
Figure 33:
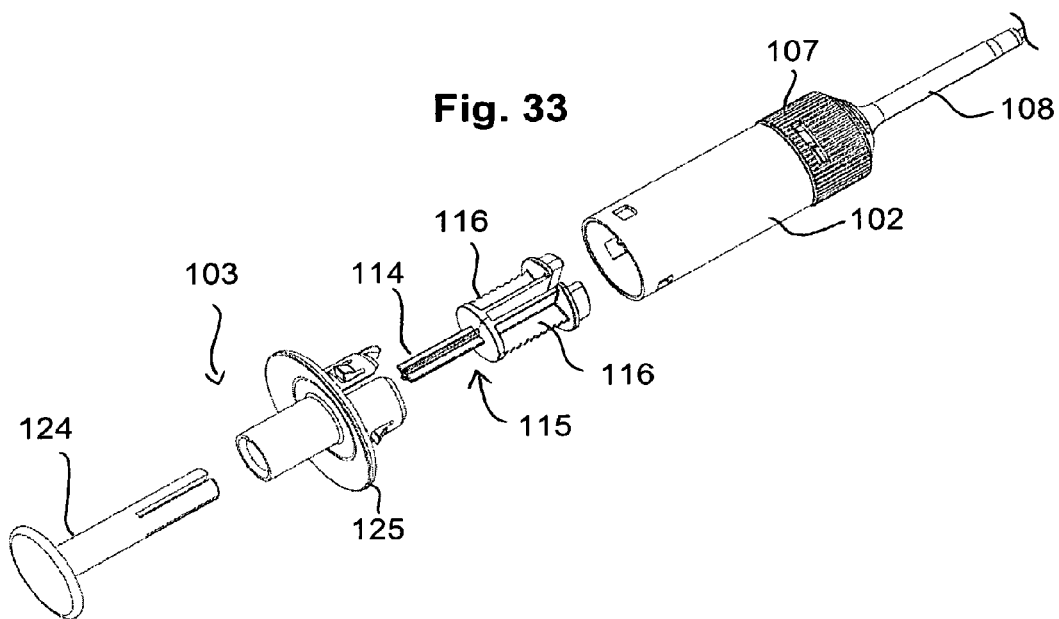
Figure 34:
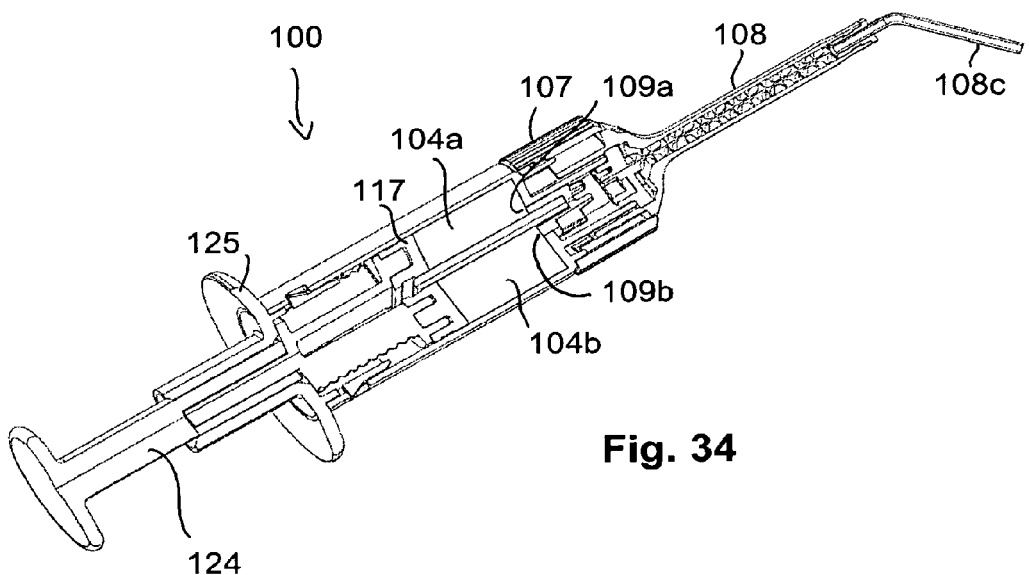
Figure 35:
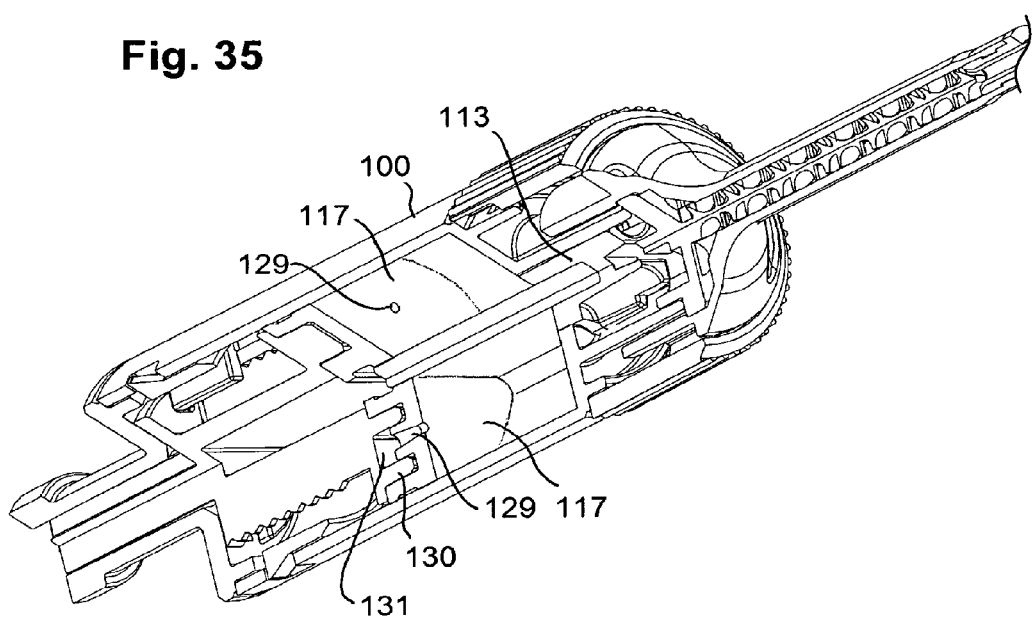

In the figures:

FIG. 1 schematically shows a dispensing device according to the invention in accordance with a first embodiment in a perspective view, FIG. 2 schematically shows a longitudinal section through the dispensing device according to FIG. 1, FIG. 3 schematically shows an exploded view of the dispensing device according to FIG. 1, FIG. 4 schematically shows a further longitudinal section through the dispensing device according to FIG. 1 in a closed state, FIG. 5 schematically shows a longitudinal section view through the dispensing device according to FIG. 4 in an opened state, FIG. 6 schematically shows a view onto the distal end of the container of the dispensing device according to FIG. 1, FIG. 7 schematically shows a perspective view of the dispensing device according to FIG. 1 with the mixer removed, FIG. 8 schematically shows a perspective view of the locking ring of the dispensing device according to FIG. 1, FIG. 9 schematically shows the dispensing device according to FIG. 1 in an enlarged representation without the locking ring, FIG. 10a schematically shows, in sections, a longitudinal section through the dispensing device according to FIG. 1 in the position which frees the mixer, FIG. 10b schematically shows, in sections, a longitudinal section through the dispensing device according to FIG. 1 in the position which locks the mixer in place, FIG. 11a schematically shows a cross section through the locking ring of the dispensing device according to FIG. 1 in the position which frees the mixer, FIG. 11b schematically shows a cross section through the locking ring of the inventive dispensing device according to FIG. 11a in the position which locks the mixer in place, FIG. 12 schematically shows a dispensing device according to the invention in accordance with a second embodiment in a partially cut away exploded view, FIG. 13a schematically shows a longitudinal section through the dispensing device according to FIG. 12 in the position which frees the applicator, FIG. 13b schematically shows a longitudinal section through the dispensing device according to FIG. 12 in the position which locks the applicator in place, FIG. 14 schematically shows a dispensing device according to the invention in accordance with a third embodiment in a partially cut away perspective view, FIG. 15 schematically shows the dispensing device according to FIG. 14 in an exploded view, FIG. 16 schematically shows a dispensing device according to the invention in accordance with a fourth embodiment in a partially cut away perspective view, FIG. 17 schematically shows the dispensing device according to FIG. 16 in an exploded view, FIG. 18 schematically shows a dispensing device according to the invention in accordance with a fifth embodiment in a partially cut away perspective view, FIG. 19 schematically shows the dispensing device according to FIG. 18 in an exploded view, FIG. 20 schematically shows a longitudinal section through the dispensing device according to FIG. 18 with the mixer removed, FIG. 21 schematically shows a dispensing device according to the invention in accordance with a sixth embodiment in a partially cut away perspective view, FIG. 22 schematically shows the dispensing device according to FIG. 21 in an exploded view, FIG. 23 schematically shows a longitudinal section through the dispensing device according to FIG. 21 with the mixer removed, FIG. 24 schematically shows a dispensing device according to the invention in accordance with a seventh embodiment in a perspective view, FIG. 25 schematically shows the dispensing device according to FIG. 24 in a partially cut away perspective view, FIG. 26 schematically shows the dispensing device according to FIG. 24 in an exploded view, FIG. 27 schematically shows a longitudinal section through the dispensing device according to FIG. 24 with the mixer removed, FIG. 28a schematically shows a longitudinal section view through part of the dispensing device according to FIG. 24 in a closed state, FIG. 28b schematically shows a longitudinal section view through part of the dispensing device according to FIG. 24 in an opened state, FIG. 29 schematically shows the sealing plunger of the dispensing device according to FIG. 24 in a perspective view, FIG. 30 schematically shows a container according to the invention in accordance with an eighth embodiment in a perspective view, FIG. 31 schematically shows the container according to FIG. 30 in an exploded view, FIG. 32 schematically shows a sectional view of the container according to FIG. 30, FIG. 33 schematically shows a container according to the invention in accordance with a ninth embodiment in an exploded view, FIG. 34 schematically shows a sectional view of the container according to FIG. 33, and FIG. 35 schematically shows a container according to the invention in accordance with a tenth embodiment in a sectional view.

The dispensing device 1 illustrated in FIGS. 1 to 11b essentially consists of two containers 2a and 2b, a mixer 3 which can be replaceably fixed to the containers, a locking ring 4 for locking the mixer 3, as well as a plunger rod arrangement 5. In the text that follows, the mixer-side end of the dispensing device 1 is termed the distal end and the opposite end of the dispensing device 1, on which the plunger rod arrangement 5 is provided, is termed the proximal end.

The two containers 2a and 2b which can have different cross sections and therefore different volumes, in this case form, together with the plunger rod arrangement 5, a double-chambered syringe with which components, preferably components for producing a hardenable dental product, accommodated in the containers can be discharged in a manner known per se by advancing the plunger rod arrangement. In the embodiment shown, the containers 2a and 2b are configured as essentially cylindrical cartridges which are connected with one another by a handle 6 at their proximal end as well as by a common faceplate 7 at their distal end. Each of the containers 2a and 2b has an opening at its proximal end, through which the plunger rod arrangement 5 is introduced into the containers 2a and 2b. On the opposite side, that is to say at the distal end, the containers are provided with discharge openings 8a and 8b, which are configured as tubes which extend beyond the faceplate 7 in the distal direction.

The plunger rod arrangement 5 has two plunger rods 5a and 5b which are integrally connected with one another and which carry a discharge plunger 9a or 9b at their respective distal end. The discharge plungers 9a and 9b are in this case synchronously and sealingly displaceable in the cylindrical containers 2a and 2b. As can be seen, for example, from FIGS. 1 and 2, a control rod 10 with a plurality of notches is provided between the two plunger rods 5a and 5b and extends between and through the containers 2a and 2b, parallel to the plunger rods 5a and 5b. A catch hook 11 with a point is provided between the two containers 2a and 2b on the handle 6, which catch hook is fixed to the handle 6 and the containers 2a, 2b in such a manner that the point of the catch hook 11 engages into the notches of the control rod 10 and is pushed out of the notches of the control rod 10 when the control rod arrangement 5 is advanced, in order to lock into the next notch. On the one hand, this enables a certain safeguard against an inadvertent displacement of the plunger rod arrangement 5 relatively to the containers 2a, 2b. On the other hand, the user receives a tactile and/or audible feedback in the case of a displacement of the plunger rod arrangement, which feedback allows dosing of a certain quantity of the components to be discharged from the containers 2a, 2b. Additionally, a scale (not depicted) which is assigned to the control rod 10 can be provided on the containers 2a, 2b in such a manner that the quantity of the components which has already been discharged from the containers 2a, 2b and/or the residual quantity which is contained in the same can be read off by means of the position of the control rod 10.

In the FIGS. 1 to 3, the notches on the control rod 10 and the raised parts between the same are configured uniformly, that is to say have the same depth and height respectively. In deviation from the representation in FIGS. 1 to 3, the first raised part, which the point of the catching hook 11 must pass during the first use of the dispensing device 1, can be configured to be shallower or not be present at all on the control rod 10, in order to achieve a greater installation tolerance on the one hand and to reduce the initial resistance when discharging the components from the containers on the other hand. A configuration of this type is indicated in FIG. 35 which is explained in more detail below. In development of this idea, the second raised part, which the point of the catching hook 11 must pass during the first use of the dispensing device 1, can be configured to be steeper or larger on the control rod 10, in order to counter an initially large force for discharging the components from the containers with resistance. In this manner, too large a quantity of the components can be prevented from inadvertently being discharged out of the containers in the event of a sudden release of the discharge plungers 9a, 9b during the first use of the dispensing device 1.

As can be seen in particular from FIGS. 4 and 5, a peg-shaped projection 12 is provided in the discharge openings 8a and 8b in each case, which is configured integrally with the containers 2a, 2b and the tubes which form the discharge openings 8a, 8b. The peg-shaped projections 12 extend in this case only in a small proximal region of the discharge openings 8a, 8b, while the remaining distal region of the tubes of the discharge openings 8a, 8b is, at first, empty. An annular space is thereby formed between the inner wall of the tubes of the discharge openings 8a, 8b and the outer surface of the peg-shaped projections 12, through which space the components accommodated in the containers 2a, 2b can be discharged.

In order to be able to seal the containers 2a, 2b during transporting and storage, a sealing plunger 13 is placed onto each of the peg-shaped projections 12. The sealing plungers 13 are configured as rings or small tubes which close the annular interspace between the outer surface of the peg-shaped projections 12 and the inner surface of the tubes of the discharge openings 8a, 8b in a sealing manner. At the same time, the sealing plugs 13 are displaceably mounted in the tubes of the discharge openings 8a, 8b. It is thereby possible to displace the sealing plungers 13 in the distal direction, out of their position according to FIG. 4, which seals the containers 2a, 2b, into the opened position according to FIG. 5.

This displacement of the sealing plugs 13 takes place in that pressure is exerted on the components accommodated in the containers 2a, 2b by the plunger rod arrangement 5 and the discharge plungers 9a, 9b. As soon as this pressure is sufficiently high, the sealing plugs 13 are pushed away, in the distal direction, from the peg-shaped projections 12, so that the components can flow out, first through the annular space around the peg-shaped projections 12 and through the central opening in the sealing plungers 13 and out of the containers 2a, 2b. The length of the tubes which form the discharge openings 8a, 8b is, in this case, dimensioned in such a manner that it is bigger than the length of the peg-shaped projections 12 and the sealing plungers 13 combined. This has the effect that the sealing plungers 13 can be completely detached from peg-shaped projections 12 and displaced in the distal direction.

The mixer 3 is configured as a static mixer in the embodiment shown and essentially consists of a housing 14 and a mixer helix 15. The dispensing device 1 according to the invention can basically also have a dynamic mixer, however.

The housing 14 of the mixer 3 consists of a, for example, cylindrical tube 14a which defines a mixing chamber in which the mixer helix 15 is accommodated and, at the distal end of which, an outlet opening 16 is formed. The cylindrical tube 14a of the housing 14 merges, by means of a flange 14b, into an oval section 14c which can be inserted into the locking ring 4 to connect the mixer 3 with the containers 2a, 2b.

The mixer helix 15 accommodated in the housing 14 is configured integrally with two cylindrical connecting pieces 17a, 17b which define inlet openings for the components discharged from the containers 2a, 2b. The size of the inlet openings 17a, 17b is, in this case, adapted to the size of the discharge openings 8a, 8b in such a manner that the connecting pieces of the inlet openings 17a, 17b can be put into the tubes of the discharge openings 8a, 8b in a sealing manner. Alternatively, the tubes 8a, 8b can be put into the inlet openings. The connecting pieces 17a, 17b in this case only extend into the tubes of the discharge openings 8a, 8b in a small region in order to enable the sealing plugs 13 to release themselves from the peg-shaped projections 12 completely. The connecting pieces of the inlet openings 17a, 17b can, in this case, form a stop for the sealing plugs 13, in order to limit their movement in the distal direction.

The connecting pieces (sockets) of the inlet openings 17a, 17b and the mixer helix 15 are configured in a manner known per se so that the components discharged from the containers 2a, 2b are conveyed separately from one another as far as into the cylindrical tube 14a of the housing, in the mixing space of which tube, the two components are mixed with one another by a multiplicity of mixer spirals of the mixer helix 15, before these two components escape, mixed with one another, from the mixer 3 through the outlet opening 16.

As can be seen particularly clearly from the representation in FIG. 9, two spring arms 18 are formed on the faceplate 7 of the containers 2a, 2b, which extend in the distal direction essentially parallel to the tubes of the discharge openings 8a, 8b. The spring arms 18 are, in this case configured integrally with the containers 2a, 2b and the faceplate 7. The length of the spring arms 18 approximately corresponds in this case to the height of the oval section 14c of the housing 14 of the mixer 3. The spring arms 18 are configured in such a manner in each case, that although they are firmly connected with the faceplate 7, their free ends 19 which face away from the faceplate 7 can be elastically pivoted in a radial direction. In other words, the free ends 19 of the spring arms 18 can be pivoted radially inwards, that is to say towards each other, or radially outwards, that is to say away from each other.

Each of the spring arms 18 bears, in the region of its free end 19, a radially inwards facing rib 20, which defines a stop face which faces towards the containers, that is to say in the proximal direction. A corresponding catch 21 is formed on two mutually opposite sides on the oval section 14c of the housing 14 of the mixer 3, which catch defines a stop face which faces in the distal direction. The dimensions of the housing 14 and of the spring arms 18 is selected to be such in this case that the mixer 3 can be put onto the containers 2a, 2b in the unloaded state of the spring arms 18 which is shown in FIGS. 9, 10a and 11a, wherein the catches 21 can pass the ribs 20 of the spring arms 18 without deforming the spring arms 18. In this state, the mixer 3 may also allow itself to be taken off the containers 2a, 2b again, as the ribs 20 of the spring arms 18 do not come into contact with the catches 21 of the mixer 3.

A catch 22 is provided, in each case, on the outer side of each spring arm 18, in the region of the faceplate 7. This catch is configured in such a manner in this case, that it defines a stop face which faces in the proximal direction. These catches 22 of the spring arms 18, serve to fix the locking ring 4 to the containers 2a, 2b.

The locking ring 4 has two slot-shaped recesses 23 for this purpose, as can be seen, e.g., from the representations of FIGS. 8, 10a and 10b, which recesses are configured and arranged in such a manner that the locking ring 4 can be secured onto the spring arms 18. Insertion surfaces 24 are configured, in the form of groove-like depressions, in the locking ring 4 for a defined installation of the latter, which insertion surfaces run from the proximal front face of the locking ring 4 to laterally adjacent to the slot-shaped recesses 23 and form guide surfaces for the catches 22. As shown in FIGS. 10a and 10b, the catches 22 of the spring arms 18 engage into the slot-shaped recesses 23 in the locking ring 4. The locking ring 4 is thereby held axially fixedly, that is to say captively, on the containers 2a, 2b and can be turned relatively to the latter. The amount of maximum possible rotational movement is, in this case, defined by the length of the slot-shaped recesses 23 and the width of the catches 22. In the embodiment shown, the length of the slot-shaped recesses 23 approximately corresponds to double the width of a catch 22. Turning the locking ring 4 through approximately 90° is therefore possible.

As shown in FIG. 8, a catch projection 25 is provided in the centre of the slot-shaped recess 23. This catch projection 25 forms a lock which impedes turning of the locking ring 4 relatively to the containers 2a, 2b. The catches 22 of the spring arms 18 can, however, get past the catch projection 25, wherein a user receives a tactile feedback which shows that the locking ring 4 has reached one of its two rotational end positions. If the slot-shaped recesses 23 are configured longer than in the embodiment shown, two catch projections 25 can be provided, which define the two rotational end positions of the locking ring 4.

As can be drawn from the FIGS. 8, 9 and also 11a and 11b, guide webs 26 are formed on the faceplate 7 of the containers 2a, 2b, which run between the two spring arms 18 in an approximately bow-shaped manner in each case. These guide webs 26, which run in an arc-shaped manner, have an external diameter which approximately corresponds to the internal diameter of the locking ring 4. In this manner, the locking ring 4 is, in addition to the lower section of the spring arms 18, also held, in a rotationally guided manner, on the faceplate 7 of the containers 2a, 2b by means of the guide webs 26. The guide webs 26 in this case prevent the locking ring 4 from being pushed radially inwards in the region between the spring arms 18, as a result of which pushing in, the locking ring 4 could be deformed in such a manner that it is undesirably detached from the spring arms 18. The guide webs 26 therefore allow a captured fixing of the locking ring 4 to the containers 2a, 2b.

An assembly lock is shown in the FIGS. 8, 9 and 11a, 11b, which prevents the locking ring 4 from being non-destructively uninstalled after its installation on the containers 2a, 2b. The assembly lock has two disassembly fingers 27 which are, in each case, formed on an end of the guide webs 26 in such a manner, that the disassembly fingers 27 extend away from the faceplate 7 of the containers 2a, 2b in the axial direction. The assembly lock further comprises two disassembly ribs 28 which are provided on the inner side of the locking ring 4, adjacent to the insertion surfaces 24. The two disassembly ribs 28 are configured in an essentially wedge-shaped manner in this case, wherein a locking surface which extends radially inwards is provided in direct adjacency to the side of the insertion surfaces 24 which faces away from the slot-shaped recess 23 in each case. A bevelled surface of the disassembly ribs 28, starting from the locking surface, gradually draws close to the inner contour of the locking ring 4, which is cylindrical in certain areas.

When putting the locking ring 4 onto the spring arms 18 these surfaces slide with the catches 22 in the insertion surfaces 24, wherein the disassembly ribs 28 are positioned in a space between the spring arms 18 and the disassembly fingers 27. If the locking ring 4 is then rotated, then the disassembly fingers 27 slide over the bevelled surface of the disassembly rib and snap behind it, while, at the same time, the catches 22 of the spring arms 18 slide into the slot-shaped recesses 23. A non-destructive backwards rotation of the locking ring 4 is prevented by the locking surfaces of the disassembly ribs 28, which then come into contact with the disassembly fingers 27. The locking ring 4 is therefore fixed on the containers in a captured manner.

Guiding grooves 29 are provided on the inner side of the locking ring 4 in the region of its distal end and on mutually opposite sides in each case. These guiding grooves 29 run in an arc, whose distance from the axis of rotation of the locking ring 4 is not constant. The free end 19 of the spring arms 18 is in each case configured as a projection which is shaped to fit to the guiding groove 29.

As can be seen from the representation of FIGS. 10a and 11a and 10b and 11b, the projection of the free end 19 of the spring arms 18 engages into the respective guiding groove 29 of the locking ring 4 when the locking ring 4 is secured onto the spring arms 18. In FIGS. 10a and 11a, the position of the locking ring 4 is, in this case, shown, in which the free ends 19 of the spring arms 18 engage into the radially most outlying region of the guiding groove 29.

If the locking ring 4 is then turned relatively to the containers 2a, 2b and therefore to the spring arms 18, the free ends 19 of the spring arms 18 are pushed radially inwards within the guiding groove 29. This is shown in the FIGS. 10b and 11b. The ribs 20 of the spring arms 18 thereby grip behind the catches 21 on the mixer 3. Thus, the mixer 3 is held firmly on the containers 2a, 2b in the axial direction. The controlling of the free ends 19 of the spring arms 18 in the guiding grooves 29 additionally prevents the spring arms 18 from being pushed radially outwards in such a manner, that the ribs 20 come out of engagement with the catches 21. An unintentional releasing of the connection between the mixer and the containers can hereby be prevented.

Only by rotating the locking ring 4 in the opposite direction are the free ends 19 of the spring arms 18 moved radially outwards again into the position shown in FIGS. 10a and 11a, so that the mixer 3 is freed. The rotating of the locking ring 4 relatively to the containers 2a, 2b therefore brings about a very reliable locking of the mixer 3 on the containers or a freeing of the mixer, so that the latter can be removed from the containers 2a, 2b. The locking ring 4 in this case remains on the containers 2a, 2b as a result of the securing in place with the spring arms 18.

The locking ring 4 has a central opening, through which the oval section 14c of the mixer housing 14 can be passed. This opening is adapted to the outer contour of the oval section 14 in such a manner, that the mixer 3 can only be put onto the containers 2a, 2b if the locking ring 4 is orientated in its position shown in the FIGS. 10a and 11a. In this position, the inlet openings 17a, 17b also engage into the discharge openings 8a, 8b.

Further embodiments of the invention are shown in the FIGS. 12 to 29. Parts which are similar with the previously described components of the dispensing device 1 are designated with the same reference numerals.

A further embodiment of a dispensing device 1 according to the invention, in which, however, only one container 2 is provided, is shown in FIGS. 12, 13a and 13b. A central discharge opening 8 is provided on a faceplate 7 of this container 2, in which opening, a sealing plunger 13 is held on a peg-shaped projection 12, in order to seal the container 2 in its position shown in FIG. 13a. The sealing plunger 13 can, by means of the internal pressure of the component contained in the container 2, be displaced forwards in the axial direction into the position shown in FIG. 13b, whereby the container is opened.

The coupling means of the dispensing device according to FIGS. 12 to 13b essentially has a construction identical to that described previously with reference to the FIGS. 1 to 11b. Correspondingly, spring arms 18 and guide webs 26 and also disassembly fingers 27 are provided on the front side of the container 2, in order to fix a locking ring 4 to the container 2 such that it can be rotated, but not axially released. Instead of a mixer, an applicator 30 is provided in the form of a discharge spout in the embodiment according to the FIGS. 12 to 13b. The applicator 30 can be fixed to the container 2 by means of the locking ring 4, as described above for the mixer 3 with reference to the FIGS. 1 to 11b.

A third embodiment of a dispensing device according to the invention is shown in FIGS. 14 and 15, in which again two containers 2a and 2b are provided. The containers 2a and 2b are, in this case, not arranged next to one another as described above with reference to the FIGS. 1 to 11b, but rather concentrically to one another. The discharge openings of the two containers 2a, 2b in this case open into a common discharge connecting piece 31, in which, in a manner similar to that of the previously described embodiment, only a single sealing plunger 13 is provided. This sealing plunger seals both discharge openings of the containers 2a, 2b in its state represented in FIG. 14 and can be pushed forwards in the axial direction in such a manner, by means of the internal pressure of the component in the outer annular container 2a, that both discharge openings are freed.

The mixer 3 shown in the FIGS. 14 and 15 essentially corresponds, both in terms of its construction and in terms of its connection with the containers 2a, 2b by means of the coupling means with the locking ring 4, to the construction described previously with reference to the FIGS. 1 to 11b. However, the mixer 3 according to the FIGS. 14 and 15 only has one inlet opening 17, which is adapted for connection to the discharge connecting piece 31.

The dispensing device according to FIGS. 14 to 15 further has a plunger rod arrangement which is not shown in the figures, with which the components can be dispensed from the containers 2a and 2b together.

The dispensing device is also provided with two containers 2a, 2b in the embodiments shown in FIGS. 16 and 17, which containers are, however, arranged next to one another and are, in each case, shaped approximately semi-circularly in cross section. The two containers 2a, 2b therefore together form a housing which is approximately circular in cross section and is divided by a separating wall 32.

The discharge openings of the two containers 2a, 2b in turn open into a common discharge connecting piece 31, in which, a single sealing plunger 13 is provided for sealing the two containers. The connection of the mixer 3 corresponds to the embodiments described above with reference to the FIGS. 1 to 11b and 14 and 15.

While the dispensing devices portrayed in the previously described embodiments are essentially configured as a syringe, embodiments will be described hereinbelow, which are constructed as capsule-shaped mini-cartridges, what are known as PLTs (pre-loaded tips). Mini-cartridges of this type are particularly suitable for use in discharge devices which have an advanceable plunger (tappet) for discharging the components contained in the mini-cartridges.

FIGS. 18 to 20 show a further embodiment of a dispensing device according to the invention, which has two containers 2a, 2b, which are arranged one behind the other when viewed in an essentially axial direction. The first container 2a is formed by a plunger 33, which is cylindrical in sections, and a discharge insert 34. The second container 2b is essentially delimited by the housing of the dispensing device itself, in which the cylindrical plunger 33 is also guided in a displaceable manner, and a plunger 35, which surrounds the discharge insert 34 in an annular manner.

The discharge openings of the two containers 2a, 2b open into a common discharge connecting piece (socket) 31. A sealing plunger 13 is provided in the discharge connecting piece, which seals the discharge openings in the position according to FIG. 18 and can be pushed forwards in the axial direction, that is to say, towards the mixer 3, within the discharge connecting piece 31 by the pressure of the component contained in the container 2b, in order thereby to open both discharge openings of the containers 2a and 2b.

The mixer 3 is, in this embodiment, fixed to the containers by means of a coupling means which comprises a locking ring 4, as described above.

In order to dispense the components contained in the containers 2a, 2b, the cylindrical plunger 33 is pushed forward in the direction of the mixer 3. The volume in the container 2a is, on the one hand, thereby reduced so that the component accommodated therein is delivered through the discharge insert 34 to the discharge connecting piece 31, while at the same time an axially forward front face of the cylindrical plunger 33 pushes the plunger 35 forwards so that the volume of the container 2b is also reduced and the component accommodated therein is likewise delivered to the discharge connecting piece 31.

As can be seen in FIGS. 18 and 20 in particular, the plunger 35 is sealed with respect to the outer cylindrical housing wall of the two containers by means of a sealing ring. In the same manner, the discharge insert 34 is sealed with respect to the cylindrical plunger 33 by means of a sealing ring.

An embodiment which is similar to the above-described embodiment in terms of the construction of the dispensing device is shown in the FIGS. 21 to 23. The discharge openings of the two containers 2a, 2b, which are in turn arranged one behind the other, do not however open into a common discharge connecting piece 31 here, but rather, in a manner similar to the embodiment according to the FIGS. 1 to 11b, two separate discharge openings 8a, 8b are provided, which are respectively sealed by two separate sealing plungers 13. Owing to the central arrangement of the discharge insert 34, an eccentric arrangement of the discharge opening 8b for the component accommodated in the container 2b is produced. The mixer 3 is also correspondingly placed eccentrically on the two containers. The coupling arrangement for releasable connection of the mixer 3 is also eccentrically arranged in the same manner.

A further embodiment of a dispensing device configured as a mini-cartridge is shown in the FIGS. 24 to 29. The mini-cartridge is again configured with a housing, which is essentially cylindrical, and a lid which seals the housing at the back and can be locked in place on the housing. Two chambers, which each have an approximately semi-circular cross section and define the containers 2a and 2b, are formed within the housing. The volume of the containers can be reduced in a defined manner by means of a plunger rod arrangement 5, which extends partially through the lid, which is secured in place on the housing, and partially projects into the two containers 2a, 2b. A coupling means with a locking ring 4 for releasably fixing a mixer 3 is in turn provided on the front side of the containers 2a, 2b which faces away from the lid, wherein the coupling means essentially has the construction described previously and the functioning described previously with the spring arms 18 which can be moved radially inwards and radially outwards by rotating the locking ring.

The two adjacently arranged containers 2a, 2b each have a discharge opening 8a, 8b, which open into a common discharge connecting piece 31, which is configured to have an approximately oval cross section in the embodiment shown. The mixer 17 is correspondingly provided with an inlet opening, which is likewise essentially oval-shaped to be able to be inserted into the discharge connecting piece 31. The inlet opening 17 is subdivided into two sections by a separating element so that the components which are discharged from the containers 2a, 2b can be guided separately from each other as far as the mixer helix 15 of the mixer, as described in more detail below.

In the delivery state shown in FIG. 25, the two containers 2a, 2b are sealed by a sealing plunger 13'. The sealing plunger 13' shown in detail in FIG. 29 has two sealing blocks 36 which project backwards from a transverse wall, that is away from the mixer 3, the outer contour of which sealing blocks is matched to the inner contour of the discharge openings 8a, 8b. In the illustration according to FIG. 28a, the sealing blocks 36 project into the discharge openings 8a, 8b and seal them. A gap-like space is formed between the two sealing blocks 36, which space is matched to the rectangular contour of a separating wall 37 which is provided between the two discharge openings 8a, 8b within the discharge connecting piece 31. The sealing plunger 13' can thus be displaced in a guided manner on the separating wall 37 from the closed position shown in FIG. 28a and axially forwards into the opened position shown in FIG. 28b, by means of which the two discharge openings 8a, 8b are freed. The components can thus flow from the containers 2a, 2b through the discharge openings 8a, 8b and past the sealing plunger 13' into the discharge connecting piece 31.

In order to allow the sealing plunger 13' to be displaced on the separating wall 37, a ventilation opening is provided in the transverse wall of the sealing plunger 13', and semi-circular ventilation channels are likewise formed in the sealing blocks 36 adjacent to the space which accommodates the separating wall 37 in the closed state. This means that the sealing plunger 13' can be set and pushed on the separating wall 37. Projections are formed on the sealing plunger 13' on the side opposite the two sealing blocks 36, which projections interact with the inlet opening 17 of the mixer 3 in such a manner that the components discharged from the containers 2a, 2b are directed separately from each other to the mixer helix 15 of the mixer 3.

The previously described embodiments show dispensing devices for one or two components accommodated in corresponding containers. In principle, more than two containers can also be provided in order to discharge a greater number of different components. The various arrangements of the containers can be combined among one another.

A further embodiment of the invention is shown in FIGS. 30 to 32, wherein the basic structure of the container corresponds to that according to FIGS. 19 to 28. FIGS. 30 to 32 shows a container 100 configured as a mini-cartridge. The mini-cartridge is again configured with a housing 102, which is essentially cylindrical on the inside and the outside, and a lid 103, which seals the housing at the back and can be secured in place on the housing. Two chambers 104a and 104b (FIG. 34), which each have an approximately semi-circular cross section, are formed within the housing. The volume of the chambers can be reduced in a defined manner by means of a plunger rod arrangement 115, which extends partially through the lid 103, which is secured in place on the housing 102, and partially projects into the two chambers 104a, 104b.

A coupling means 106 with a locking ring 107 for releasable fixing of a mixer 108 is provided on the front side of the chambers 104a, 104b, which faces away from the lid 103. The locking ring 107 is secured firmly in place on the container 100 and can be rotated relative to the container 100 between a position which frees the coupling means 106 for installing or uninstalling the mixer 108 and a position which blocks the coupling means 106, in which the mixer 108 is locked firmly in place on the container 100, as is described in more detail above with reference to the FIGS. 1 to 29.

The mixer 108 is configured in the embodiment shown as a discharge tube 108a with a mixer helix 108b, that is as a static mixer. In the delivery state of the container 100 shown in FIG. 30, the mixer 108 is already pre-installed on the container 100 in such a manner that the container can be put into use without further installation steps.

The two adjacently arranged chambers 104a, 104b each have a discharge opening 109a, 109b, which open into a common discharge connecting piece (socket) 110, which is configured to have an approximately oval cross section in the embodiment shown. The mixer 108 is correspondingly provided with an inlet opening, which is likewise essentially oval-shaped to be able to be inserted into the discharge connecting piece 110. The inlet opening is subdivided into two sections by a separating element so that the components which are discharged from the chambers 104a, 104b can be guided separately from each other as far as the mixer helix 108b of the mixer, as described in more detail below.

In the delivery state, the two chambers 104a, 104b are sealed by a sealing plunger 111, which has two sealing blocks which project backwards from a transverse wall, that is away from the mixer 108, the outer contour of which sealing blocks is matched to the inner contour of the discharge openings 109a, 109b. A gap-like space is formed between the two sealing blocks, which space is matched to the rectangular contour of a separating wall 112 which is provided between the two discharge openings 109a, 109b within the discharge connecting piece 110. The sealing plunger 111 can thus be displaced in a guided manner on the separating wall 112 from a closed position and axially forwards into the discharge connecting piece 110, into an opened position, by means of which the two discharge openings 109a, 109b are freed. The components can thus, as explained with reference to the FIGS. 18 to 29, flow from the chambers 104a, 104b through the discharge openings 109a, 109b and past the sealing plunger 111 into the discharge connecting piece 110 and into the mixer 108. In this case, the components are guided separately from one another in the chambers and along the sealing plunger 111 until they reach the mixer. This prevents contamination of the components within the channels and therefore enables a reuse of the container.

The lid 103 of the container 100 is provided with a retaining section 113 which is central in the embodiment shown and projects away from the container on the side facing away from the mixer 108. The retaining section has a first, approximately cylindrical region 113a and a second region 113b, which faces away from the mixer 108 and has an outer diameter which is enlarged in a flange-like manner with respect to the first region 113a. The retaining section 113 is thus suitable for fixing the container in a discharge gun according to EP 1 256 389 A2.

The retaining section 113 is provided with a through-opening, in which a plunger rod 114 of a transfer tappet 115 is displaceably guided in such a manner that the plunger rod 114 is provided flush with the front side of the second region 113b in the delivery state. The transfer tappet 115 has two actuation sections 116, which are each assigned to a chamber 104a, 104b. The two actuation sections 116, which are at a distance from each other, project in the direction of the mixer 108 away from the plunger rod 114 into the chambers, in which discharge plungers 117 are accommodated in a displaceable manner. The transfer tappet 115 has the effect of pushing the discharge plungers 117 of both chambers 104a, 104b forwards at the same time when the plunger rod 114 is pushed into the through-opening of the retaining section 113.

A window 122 is provided in the housing 102, which housing in this embodiment consists of an opaque material, in the rear region which faces away from the mixer 108, which window extends in the axial direction of the container. A marking element 123, for example a coloured dot or projection, is assigned to the window 122 on the transfer tappet 115 in such a manner that the marking element 123 is visible through the window 122 from the outside. If the transfer tappet 115 is now pushed in order to discharge the components in the container 100, then the position of the marking element 123 in the window 122 changes and thereby allows the filling level of the container to be monitored. To this end, the window 122 is provided with a scale.

Since the chambers in which the, for example, light-sensitive components are accommodated are sealed by the discharge plunger 117 in the direction of the window 122, the storage stability of the components is not adversely affected by the window 122.

In order to allow the marking element 123 to be inspected in the window 122 over the entire displacement path of the transfer tappet 115, the fixing of the lid 103 to the housing 102 is changed in such a manner compared to the embodiments according to FIGS. 18 to 28 that the lid 103 does not grasp the housing but can be pushed into it and secured in place there.

The mixer 108 is provided with an additional discharge tube 108c, which facilitates application of the mixture emerging from the mixer 108, for example for dental uses.

The syringe-like discharge of the components from the container 100 by means of a tappet 124 is possible in a particularly simple manner if the lid 103 has a flange-like edge 125, as shown in the embodiment according to FIGS. 33 and 34. The tappet 124 and the plunger rod 114 have contours which are matched to each other, so that the plunger rod 114 and the tappet 124 can be guided together in the sleeve-like guide section of the lid 103. In order to discharge the components, the tappet 124 is supported in such a manner that it grasps the plunger rod 114 on a wall of the transfer tappet 115, which wall connects the actuation sections 116.

In a deviation from the embodiment of FIGS. 24 to 29, the sealing plunger 113 can, as shown in FIG. 35, also be configured without a ventilation opening. In this case, the container 100 is sealed by the sealing plunger 113 before filling and then filled from the side facing away from the mixer. The discharge plungers 117 are each configured with a ventilation opening 129 so that residual air can escape through the discharge plungers 117 when they are inserted into the container 100. To seal the ventilation openings 129 of the discharge plungers 117, annular projections 130 can be formed on the front-side of the actuation sections 116 of the plunger rods, which sections are connected to the discharge plungers. The projections 130 consist essentially of a closed, circumferential wall, which encloses a hollow 131 which is open in the direction of the discharge plungers 117. The wall of each projection 130 interacts in a sealing manner with a corresponding rear wall on the discharge plungers 117, in order to seal the ventilation openings 129 in this manner. Excessive material, which may be present and have emerged from the ventilation openings 29, can be accommodated in the hollows 131.

The invention claimed is:

1. Dispensing device comprising:
   at least one essentially rigid container filled with a component to be dispensed and is closed with respect to the surroundings in a sealed manner by means of at least one sealing element,
   a coupling means for releasable fixing an applicator to the at least one container, and
   an applicator which is releasably fixed by the coupling means,
   wherein the coupling means comprises at least one spring arm,
      the at least one spring arm comprising a radially pivotable free end for locking the applicator in place on at least one container, wherein the spring arm is part of the at least one container, and
   wherein the coupling means further comprises a moveable locking ring,
   wherein the locking ring is rotatable with respect to the at least one spring arm, but not axially-displaceable.

2. Dispensing device according to claim 1 wherein at least two containers, to which a mixer, a needle, a discharge spout, a sponge or a brush is releasably fixed as an applicator.

3. Dispensing device according to claim 1, the dispensing device configured as a double-chambered syringe with two containers, which are connected integrally with one another, and a plunger rod arrangement for simultaneously advancing discharge plungers in the containers.

4. Dispensing device according to claim 1 wherein at least two containers are essentially arranged next to one another and are, in particular, configured as semi-circular containers in cross section.

5. Dispensing device according to claim 1 wherein the locking ring comprises a groove which acts together with the spring arm to control the pivot movement of the spring arm as a result of a rotation of the locking ring.

6. Dispensing device according to claim 1 wherein the applicator comprises a needle.

7. Dispensing device according to claim 1 wherein the applicator comprises a discharge spout.

8. Dispensing device according to claim 1 wherein the applicator comprises a sponge.

9. Dispensing device according to claim 1 wherein the applicator comprises a brush.

* * * * *